(12) United States Patent
Aihara et al.

(10) Patent No.: US 8,431,513 B2
(45) Date of Patent: Apr. 30, 2013

(54) PHENOLIC COMPOUND AND RECORDING MATERIAL

(75) Inventors: Toshio Aihara, Odawara (JP); Hiroshi Sakai, Ichihara (JP); Shuntaro Kinoshita, Ichihara (JP); Satoshi Kodama, Ichihara (JP); Tadahiro Kondo, Ichihara (JP); Kazumi Jyujyo, Ichihara (JP)

(73) Assignee: Nippon Soda Co., Ltd., Tokyo (JP)

( * ) Notice: Subject to any disclaimer, the term of this patent is extended or adjusted under 35 U.S.C. 154(b) by 0 days.

(21) Appl. No.: 13/261,234

(22) PCT Filed: Sep. 28, 2010

(86) PCT No.: PCT/JP2010/005813
§ 371 (c)(1),
(2), (4) Date: Mar. 27, 2012

(87) PCT Pub. No.: WO2011/039994
PCT Pub. Date: Apr. 7, 2011

(65) Prior Publication Data
US 2012/0204763 A1    Aug. 16, 2012

(30) Foreign Application Priority Data

Sep. 30, 2009  (JP) ................. 2009-227277
Mar. 30, 2010  (JP) ................. 2010-079459
Mar. 31, 2010  (JP) ................. 2010-082898

(51) Int. Cl.
B41M 5/333    (2006.01)
C07C 317/22   (2006.01)

(52) U.S. Cl.
USPC .................. 503/216; 106/31.18; 544/161

(58) Field of Classification Search ............... None
See application file for complete search history.

(56) References Cited

FOREIGN PATENT DOCUMENTS

| | | |
|---|---|---|
| JP | 05-246924 A | 9/1993 |
| JP | 06-184047 A | 7/1994 |
| JP | 08-333329 A | 12/1996 |
| JP | 10-029969 A | 2/1998 |
| JP | 10-330350 A | 12/1998 |
| JP | 2003-305959 A | 10/2003 |
| JP | 2006-327950 A | 12/2006 |

*Primary Examiner* — Bruce H Hess
(74) *Attorney, Agent, or Firm* — Foley & Lardner LLP

(57) ABSTRACT

An object of the present invention is to provide a recording material that is excellent in color-developing properties and background and image stabilities, and a compound used therein. The present invention relates to a compound represented by the formula (I) [wherein $R^{11}$ to $R^{14}$ each independently represent a halogen atom or the like; n, p, q, and r each independently represent 0 or any integer of 1 to 4; m represents 0 or any integer of 1 to 2; a represents any integer of 1 to 10; $R^2$ represents a hydrogen atom or the like; $R^3$ represents an $OR^{51}$ group or the like; and $R^{41}$ and $R^{42}$ each independently represent a hydrogen atom or the like], a composition containing the compound, a method for producing the compound, a recording material containing at least one compound represented by the formula (I), and a recording sheet having the recording material.

7 Claims, No Drawings

PHENOLIC COMPOUND AND RECORDING MATERIAL

TECHNICAL FIELD

The present invention relates to a novel phenolic compound and a recording material containing one or more phenolic compound(s).

CROSS-REFERENCE TO RELATED APPLICATIONS

The present application is a National Stage application of PCT/JP2010/005813, filed Sep. 28, 2010, which claims priority from Japanese Patent Application No. 2009-227277 issued on Sep. 30, 2009, Japanese Patent Application No. 2010-079459 issued on Mar. 30, 2010, and Japanese Patent Application No. 2010-082898 issued on Mar. 31, 2010, and the contents thereof are incorporated herein by reference in their entirety.

BACKGROUND ART

Recording materials that employ color development through the reaction between a color-forming compound and a color-developing agent allow recording in a short time using a relatively simple apparatus without performing complicated treatments such as development and fixation and are thus widely used in thermal recording paper for output recording in facsimiles, printers, etc., or pressure-sensitive copying paper or the like for forms for simultaneous multiple copying. These recording materials are required to immediately develop colors, maintain the whiteness of an uncolored part (hereinafter, referred to as a "background"), and offer the high colorfastness of colored images. Particularly, recording materials excellent in the heat resistance of the background are desired in terms of long-term storage stability. For this purpose, attempts have been made to develop color-forming compounds, color-developing agents, storage stabilizers, etc. Nevertheless, recording materials that have well-balanced, sufficiently satisfactory color-developing sensitivity, background and image stabilities, etc., have not been found yet.

The present inventors have already proposed a recording material excellent in the heat resistance of the background using a diphenylsulfone derivative as a color-developing agent (see patent document 1), a recording material excellent in the light resistance of the background using a cinnamamide compound as a color-developing agent (see patent document 2), and a recording material excellent in image stability using a compound having repeat units as a color-developing agent (see patent document 3). However, a recording material having well-balanced color-developing properties, plasticizer resistance and oil resistance of colored images, etc., remains to be obtained.

PRIOR ART DOCUMENTS

Patent Documents

Patent Document 1: Japanese unexamined Patent Application Publication No. 8-333329
Patent Document 2: Japanese unexamined Patent Application Publication No. 2003-305959
Patent Document 3: Japanese unexamined Patent Application Publication No. 10-29969

SUMMARY OF THE INVENTION

Object to be Solved by the Invention

An object of the present invention is to improve the disadvantages of conventional recording materials as described above and to provide a recording material that is excellent in color-developing properties and background and image stabilities and, particularly, exceedingly excellent in the plasticizer resistance and oil resistance of images, and a compound used therein.

Means to Solve the Object

The present inventors have conducted diligent studies on various materials used in recording materials and consequently completed the present invention by finding that a recording material having excellent color-developing properties and plasticizer resistance and oil resistance of images is obtained by using a compound having a novel structure.

Specifically, the present invention relates to
(1) a compound represented by the formula (I):

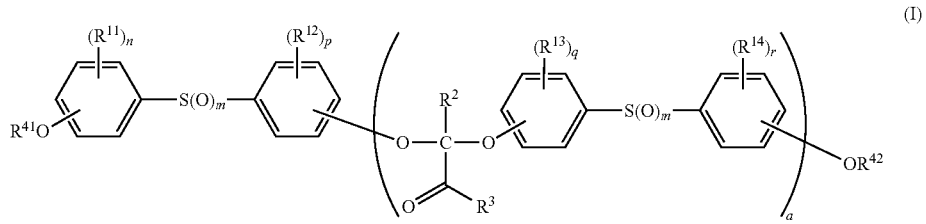

[wherein $R^{11}$ to $R^{14}$ each independently represent a halogen atom, a $C_1$-$C_6$ alkyl group, or a $C_2$-$C_6$ alkenyl group; n, p, q, and r each independently represent 0 or any integer of 1 to 4; m represents 0 or any integer of 1 to 2; a represents any integer of 1 to 10; $R^2$ represents a hydrogen atom or a $C_1$-$C_6$ alkyl group; $R^3$ represents a hydroxy group, an $OR^{51}$ group, a $NR^{52}R^{53}$ group, a $SR^{54}$ group, or OM; $R^{51}$ represents a $C_1$-$C_6$ alkyl group, a $C_2$-$C_6$ alkenyl group, an optionally substituted phenyl group, or an optionally substituted benzyl group; $R^{52}$ to $R^{54}$ each represent a hydrogen atom, a $C_1$-$C_6$ alkyl group, a $C_2$-$C_6$ alkenyl group, an optionally substituted phenyl group, or an optionally substituted benzyl group, and $R^{52}$ and $R^{53}$ together optionally form a saturated or unsaturated $C_4$-$C_{10}$ ring, which, optionally, further comprises at least one heteroatom selected from S, N, and O; M represents a metal atom; and $R^{41}$ and $R^{42}$ each independently represent a hydrogen atom, a $C_1$-$C_6$ alkyl group, a $C_2$-$C_6$ alkenyl group, or a protective group for the hydroxy group],
(2) the compound according to (1), wherein the compound represented by the formula (I) is represented by the formula (II):

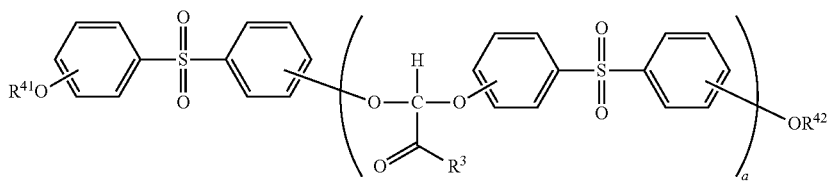

[wherein a represents any integer of 1 to 10; $R^3$ represents a hydroxy group, an $OR^{51}$ group, a $NR^{52}R^{53}$ group, a $SR^{54}$ group, or OM; $R^{51}$ represents a $C_1$-$C_6$ alkyl group, a $C_2$-$C_6$ alkenyl group, an optionally substituted phenyl group, or an optionally substituted benzyl group; $R^{52}$ to $R^{54}$ each represent a hydrogen atom, a $C_1$-$C_6$ alkyl group, a $C_2$-$C_6$ alkenyl group, an optionally substituted phenyl group, or an optionally substituted benzyl group, and $R^{52}$ and $R^{53}$ together optionally form a saturated or unsaturated $C_4$-$C_{10}$ ring, which, optionally, further comprises at least one heteroatom selected from S, N, and O; M represents a metal atom; and $R^{41}$ and $R^{42}$ each independently represent a hydrogen atom, a $C_1$-$C_6$ alkyl group, a $C_2$-$C_6$ alkenyl group, or a protective group for the hydroxy group], (3) a composition containing two or more compounds represented by the formula (I), the compounds differing in a:

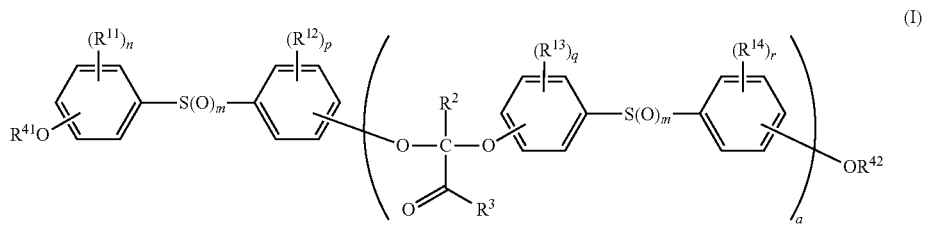

[wherein $R^{11}$ to $R^{14}$ each independently represent a halogen atom, a $C_1$-$C_6$ alkyl group, or a $C_2$-$C_6$ alkenyl group; n, p, q, and r each independently represent 0 or any integer of 1 to 4; m represents 0 or any integer of 1 to 2; a represents any integer of 1 to 10; $R^2$ represents a hydrogen atom or a $C_1$-$C_6$ alkyl group; $R^3$ represents a hydroxy group, an $OR^{51}$ group, a $NR^{52}R^{53}$ group, a $SR^{54}$ group, or OM; $R^{51}$ represents a $C_1$-$C_6$ alkyl group, a $C_2$-$C_6$ alkenyl group, an optionally substituted phenyl group, or an optionally substituted benzyl group; $R^{52}$ to $R^{54}$ each represent a hydrogen atom, a $C_1$-$C_6$ alkyl group, a $C_2$-$C_6$ alkenyl group, an optionally substituted phenyl group, or an optionally substituted benzyl group, and $R^{52}$ and $R^{53}$ together optionally form a saturated or unsaturated $C_4$-$C_{10}$ ring, which, optionally, further comprises at least one heteroatom selected from S, N, and O; M represents a metal atom; and $R^{41}$ and $R^{42}$ each independently represent a hydrogen atom, a $C_1$-$C_6$ alkyl group, a $C_2$-$C_6$ alkenyl group, or a protective group for the hydroxy group], and (4) a reaction composition containing two or more compounds represented by the formula (V),

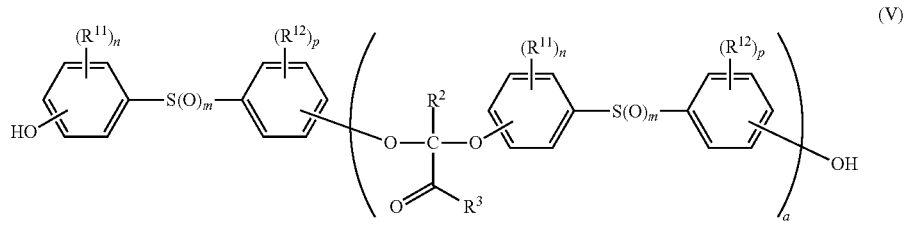

[wherein $R^{11}$ and $R^{12}$ each independently represent a halogen atom, a $C_1$-$C_6$ alkyl group, or a $C_2$-$C_6$ alkenyl group; n and p each independently represent 0 or any integer of 1 to 4; m represents 0 or any integer of 1 to 2; a represents any integer of 1 to 10; $R^2$ represents a hydrogen atom or a $C_1$-$C_6$ alkyl group; $R^3$ represents a hydroxy group, an $OR^{51}$ group, a $NR^{52}R^{53}$ group, a $SR^{54}$ group, or OM; $R^{51}$ represents a $C_1$-$C_6$ alkyl group, a $C_2$-$C_6$ alkenyl group, an optionally substituted phenyl group, or an optionally substituted benzyl group; $R^{52}$ to $R^{54}$ each represent a hydrogen atom, a $C_1$-$C_6$ alkyl group, a $C_2$-$C_6$ alkenyl group, an optionally substituted phenyl group, or an optionally substituted benzyl group, and $R^{52}$ and $R^{53}$ together optionally form a saturated or unsaturated $C_4$-$C_{10}$ ring, which, optionally, further comprises at least one heteroatom selected from S, N, and O; and M represents a metal atom]
the compounds differing in a and being obtained by reacting a compound represented by the formula (III)

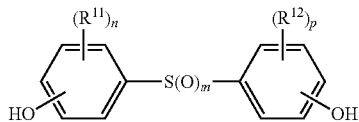

(III)

[wherein $R^{11}$ and $R^{12}$ each independently represent a halogen atom, a $C_1$-$C_6$ alkyl group, or a $C_2$-$C_6$ alkenyl group; n and p each independently represent 0 or any integer of 1 to 4; and m represents 0 or any integer of 1 to 2],
with a compound represented by the formula (IV):

$$X_2CR^2COR^3 \quad (IV)$$

[wherein each X independently represents a halogen atom; $R^2$ represents a hydrogen atom or a $C_1$-$C_6$ alkyl group; $R^3$ represents a hydroxy group, an $OR^{51}$ group, a $NR^{52}R^{53}$ group, a $SR^{54}$ group, or OM; $R^{51}$ represents a $C_1$-$C_6$ alkyl group, a $C_2$-$C_6$ alkenyl group, an optionally substituted phenyl group, or an optionally substituted benzyl group; $R^{52}$ to $R^{54}$ each represent a hydrogen atom, a $C_1$-$C_6$ alkyl group, a $C_2$-$C_6$ alkenyl group, an optionally substituted phenyl group, or an optionally substituted benzyl group, and $R^{52}$ and $R^{53}$ together optionally form a saturated or unsaturated $C_4$-$C_{10}$ ring, which, optionally, further comprises at least one heteroatom selected from S, N, and O; and M represents a metal atom].

The present invention also relates to
(5) a recording material containing a color-forming compound and at least one compound according to (1) or (2),
(6) a recording material containing a color-forming compound and at least one composition according to (3) or (4), and
(7) a recording sheet having a recording material layer formed from a recording material according to (5) or (6) on a support.

Effect of the Invention

A recording material that is excellent in background and image stabilities, further excellent in color-developing properties and exceedingly excellent in the plasticizer resistance and oil resistance of images can be obtained by using a compound of the present invention having a novel structure in a recording material containing a color-forming compound.

MODE OF CARRYING OUT THE INVENTION (Compound Represented by the Formula (I))
In the formula (I), $R^{11}$ to $R^{14}$ each independently represent a halogen atom, a $C_1$-$C_6$ alkyl group, or a $C_2$-$C_6$ alkenyl group. Specifically, examples of the halogen atom can include a fluorine atom, a chlorine atom, a bromine atom, and an iodine atom. Examples of the $C_1$-$C_6$ alkyl group can include a methyl group, an ethyl group, a n-propyl group, an isopropyl group, a n-butyl group, a sec-butyl group, a t-butyl group, an isobutyl group, a n-pentyl group, an isopentyl group, a neopentyl group, a t-pentyl group, a n-hexyl group, an isohexyl group, a 1-methylpentyl group, and a 2-methylpentyl group. Examples of the $C_2$-$C_6$ alkenyl group can include a vinyl group, an allyl group, an isopropenyl group, a 1-propenyl group, a 2-propenyl group, a 1-butenyl group, a 2-butenyl group, a 3-butenyl group, a 1,3-butanedienyl group, a 2-methyl-2-propenyl group, a n-pentenyl group, an isopentenyl group, a neopentenyl group, a t-pentenyl group, a n-hexenyl group, an isohexenyl group, a 1-methylpentenyl group, and a 2-methylpentenyl group.

$R^2$ represents a hydrogen atom or a $C_1$-$C_6$ alkyl group. Examples of the $C_1$-$C_6$ alkyl group can specifically include the same as the specific examples of $R^{11}$.

$R^3$ represents a hydroxy group, an $OR^{51}$ group, a $NR^{52}R^{53}$ group, a $SR^{54}$ group, or OM; $R^{51}$ represents a $C_1$-$C_6$ alkyl group, a $C_2$-$C_6$ alkenyl group, an optionally substituted phenyl group, or an optionally substituted benzyl group; and $R^{52}$ to $R^{54}$ each represent a hydrogen atom, a $C_1$-$C_6$ alkyl group, a $C_2$-$C_6$ alkenyl group, an optionally substituted phenyl group, or an optionally substituted benzyl group, and $R^{52}$ and $R^{53}$ together optionally form a saturated or unsaturated $C_4$-$C_{10}$ ring, which, optionally, further comprises at least one heteroatom selected from S, N, and O. M represents a metal atom. Examples of the $C_1$-$C_6$ alkyl group and the $C_2$-$C_6$ alkenyl group can specifically include the same as the specific examples of $R^{11}$ in the formula (I). Examples of the substituent for the optionally substituted phenyl group or the optionally substituted benzyl group can specifically include: a hydroxy group; halogen atoms such as a fluorine atom, a chlorine atom, a bromine atom, and an iodine atom; $C_1$-$C_6$ alkyl groups such as a methyl group, an ethyl group, a n-propyl group, an isopropyl group, a n-butyl group, a sec-butyl group, a t-butyl group, a n-pentyl group, an isopentyl group, a neopentyl group, a t-pentyl group, a n-hexyl group, an isohexyl group, a 1-methylpentyl group, and a 2-methylpentyl group; and $C_1$-$C_6$ alkoxy groups such as a methoxy group, an ethoxy group, a n-propoxy group, an isopropoxy group, a n-butoxy group, a sec-butoxy group, a t-butoxy group, an isobutoxy group, a n-pentoxy group, an isopentoxy group, a neopentoxy group, a t-pentoxy group, a n-hexoxy group, an isohexoxy group, a 1-methylpentoxy group, and a 2-methylpentoxy group. Specific examples of the ring formed by $R^{52}$ and $R^{53}$ together with N can include a pyrrolidine group, a pyrroline group, an imidazolidine group, an imidazoline group, a pyrazolidine group, a pyrazoline group, a piperidine group, a piperazine group, an indoline group, an isoindoline group, a quinuclidine group, and a morpholine group.

In OM, M represents a metal atom, and O represents an oxygen atom. Examples of M can specifically include sodium, potassium, calcium, magnesium, barium, manganese, iron, and zinc.

$R^{41}$ and $R^{42}$ each independently represent a hydrogen atom, a $C_1$-$C_6$ alkyl group, a $C_2$-$C_6$ alkenyl group, or a protective group for the hydroxy group. Specifically, examples of the $C_1$-$C_6$ alkyl group and the $C_2$-$C_6$ alkenyl group can include the same as the specific examples of $R^{11}$ in the formula (I). The protective group for the hydroxy group is a substituent that prevents the hydroxy group from being structurally altered due to various reaction conditions, and specifically refers to silyl groups such as a trimethylsilyl group and a t-butyldimethylsilyl group; acyl groups such as a benzoyl group and an acetyl group; alkyl groups such as a methyl group and a benzyl group; ether group such as a methoxymethyl group and a 2-tetrahydropyranyl group; etc.

In the compound of the present invention represented by the formula (I), $R^{13}$ and $R^{14}$ are the same as $R^{11}$ and $R^{12}$, respectively. The compound represented by the formula (I) encompasses compounds represented by the following formulas (II) and (V):

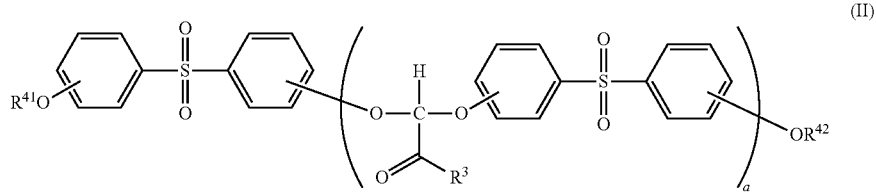

(II)

(wherein $R^3$, $R^{41}$, $R^{42}$, and $a$ are as defined in the formula (I)),
and

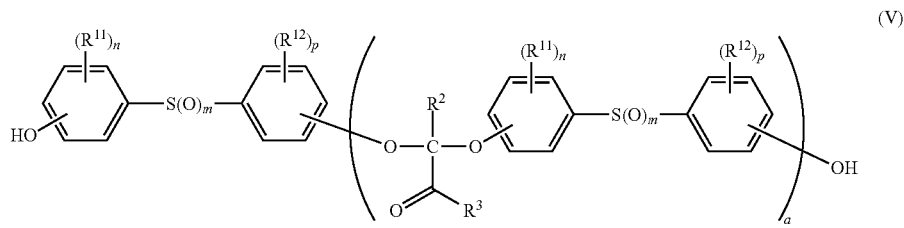

(V)

(wherein $R^2$, $R^3$, $R^{11}$, $R^{12}$, m, n, p, and a are as defined in the formula (I)).

Examples of compounds represented by the formula (I) wherein $R^{41}$ and $R^{42}$ each represent a hydrogen atom can specifically include compounds shown in Table 1. Examples of compounds represented by the formula (I) wherein $R^{41}$ and $R^{42}$ each represent a $C_1$-$C_6$ alkyl group, a $C_2$-$C_6$ alkenyl group, or a protective group for the hydroxy group can also include the same as examples shown in Table 1.

TABLE 1

Table 1(1)

(I-1)

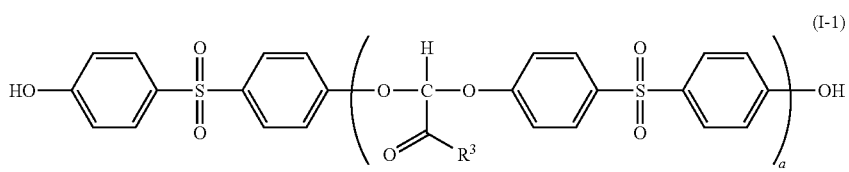

$a$ represents an integer of 1 to 10.

| No. | $R^3$ |
|---|---|
| 1 | OH |
| 2 | $OCH_3$ |
| 3 | $OCH_2CH_3$ |
| 4 | $OCH_2CH_2CH_3$ |
| 5 | $OCH(CH_3)_2$ |
| 6 | $OCH_2CH_2CH_2CH_3$ |
| 7 | $OCH(CH_3)CH_2CH_3$ |
| 8 | $OCH_2CH(CH_3)_2$ |
| 9 | $OC(CH_3)_3$ |
| 10 | $OCH_2CH_2CH_2CH_2CH_3$ |
| 11 | $OCH(CH_3)CH_2CH_2CH_3$ |
| 12 | $OCH_2CH(CH_3)CH_2CH_3$ |
| 13 | $OCH_2CH_2CH(CH_3)_2$ |
| 14 | $OC(CH_3)_2CH_2CH_3$ |
| 15 | $OCH_2C(CH_3)_3$ |
| 16 | $OCH_2CH_2CH_2CH_2CH_2CH_3$ |
| 17 | $OCH(CH_3)CH_2CH_2CH_2CH_3$ |
| 18 | $OCH_2CH(CH_3)CH_2CH_2CH_3$ |
| 19 | $OCH_2CH_2CH(CH_3)CH_2CH_3$ |
| 20 | $OCH_2CH_2CH(CH_3)_3$ |
| 21 | $OCH=CH_2$ |
| 22 | $OCH_2CH=CH_2$ |
| 23 | $OC(CH_3)=CH_2$ |
| 24 | $OCH=CHCH_3$ |
| 25 | $OCH=CHCH_2CH_3$ |
| 26 | $OCH_2CH=CHCH_3$ |
| 27 | $OCH_2CH_2CH=CH_2$ |

TABLE 1-continued

| | |
|---|---|
| 28 | OCH=CHCH=CH$_2$ |
| 29 | OCH$_2$C(CH$_3$)=CH$_2$ |
| 30 | OPh |
| 31 | OCH$_2$Ph |
| 32 | OC$_6$H$_4$-2-CH$_3$ |
| 33 | OC$_6$H$_4$-3-CH$_3$ |
| 34 | OC$_6$H$_4$-4-CH$_3$ |
| 35 | OC$_6$H$_4$-2,3-(CH$_3$)$_2$ |
| 36 | OC$_6$H$_4$-2,4-(CH$_3$)$_2$ |
| 37 | OC$_6$H$_4$-2,5-(CH$_3$)$_2$ |
| 38 | OC$_6$H$_4$-2,6-(CH$_3$)$_2$ |
| 39 | OC$_6$H$_3$-2,4,6-(CH$_3$)$_3$ |
| 40 | OCH$_2$C$_6$H$_4$-2,3-(CH$_3$)$_2$ |
| 41 | OCH$_2$C$_6$H$_4$-2,4-(CH$_3$)$_2$ |
| 42 | OCH$_2$C$_6$H$_4$-2,5-(CH$_3$)$_2$ |
| 43 | OCH$_2$C$_6$H$_4$-2,6-(CH$_3$)$_2$ |
| 44 | OCH$_2$C$_6$H$_3$-2,4,6-(CH$_3$)$_3$ |
| 45 | SCH$_3$ |
| 46 | SCH$_2$CH$_3$ |
| 47 | SCH$_2$CH$_2$CH$_3$ |
| 48 | SCH(CH$_3$)$_2$ |
| 49 | SCH$_2$CH$_2$CH$_2$CH$_3$ |
| 50 | SCH(CH$_3$)CH$_2$CH$_3$ |
| 51 | SCH$_2$CH(CH$_3$)$_2$ |
| 52 | SC(CH$_3$)$_3$ |
| 53 | SCH$_2$CH$_2$CH$_2$CH$_2$CH$_3$ |
| 54 | SCH(CH$_3$)CH$_2$CH$_2$CH$_3$ |
| 55 | SCH$_2$CH(CH$_3$)CH$_2$CH$_3$ |
| 56 | SCH$_2$CH$_2$CH(CH$_3$)$_2$ |
| 57 | SC(CH$_3$)$_2$CH$_2$CH$_3$ |
| 58 | SCH$_2$C(CH$_3$)$_3$ |
| 59 | SCH$_2$CH$_2$CH$_2$CH$_2$CH$_2$CH$_3$ |
| 60 | SCH(CH$_3$)CH$_2$CH$_2$CH$_2$CH$_3$ |
| 61 | SCH$_2$CH(CH$_3$)CH$_2$CH$_2$CH$_3$ |
| 62 | SCH$_2$CH$_2$CH(CH$_3$)CH$_2$CH$_3$ |
| 63 | SCH$_2$CH$_2$CH(CH$_3$)$_3$ |
| 64 | SCH=CH$_2$ |
| 65 | SCH$_2$CH=CH$_2$ |
| 66 | SC(CH$_3$)=CH$_2$ |
| 67 | SCH=CHCH$_3$ |
| 68 | SCH=CHCH$_2$CH$_3$ |
| 69 | SCH$_2$CH=CHCH$_3$ |
| 70 | SCH$_2$CH$_2$CH=CH$_2$ |
| 71 | SCH=CHCH=CH$_2$ |
| 72 | SCH$_2$C(CH$_3$)=CH$_2$ |
| 73 | SPh |
| 74 | SCH$_2$Ph |
| 75 | SC$_6$H$_4$-2-CH$_3$ |
| 76 | SC$_6$H$_4$-3-CH$_3$ |
| 77 | SC$_6$H$_4$-4-CH$_3$ |
| 78 | SC$_6$H$_4$-2,3-(CH$_3$)$_2$ |
| 79 | SC$_6$H$_4$-2,4-(CH$_3$)$_2$ |
| 80 | SC$_6$H$_4$-2,5-(CH$_3$)$_2$ |
| 81 | SC$_6$H$_4$-2,6-(CH$_3$)$_2$ |
| 82 | SC$_6$H$_3$-2,4,6-(CH$_3$)$_3$ |
| 83 | SCH$_2$C$_6$H$_4$-2,3-(CH$_3$)$_2$ |
| 84 | SCH$_2$C$_6$H$_4$-2,4-(CH$_3$)$_2$ |
| 85 | SCH$_2$C$_6$H$_4$-2,5-(CH$_3$)$_2$ |
| 86 | SCH$_2$C$_6$H$_4$-2,6-(CH$_3$)$_2$ |
| 87 | SCH$_2$C$_6$H$_3$-2,4,6-(CH$_3$)$_3$ |
| 88 | NHCH$_3$ |
| 89 | NHCH$_2$CH$_3$ |
| 90 | NHCH$_2$CH$_2$CH$_3$ |
| 91 | NHCH(CH$_3$)$_2$ |
| 92 | NHCH$_2$CH$_2$CH$_2$CH$_3$ |
| 93 | NHCH(CH$_3$)CH$_2$CH$_3$ |
| 94 | NHCH$_2$CH(CH$_3$)$_2$ |
| 95 | NHC(CH$_3$)$_3$ |
| 96 | NHCH$_2$CH$_2$CH$_2$CH$_2$CH$_3$ |
| 97 | NHCH(CH$_3$)CH$_2$CH$_2$CH$_3$ |
| 98 | NHCH$_2$CH(CH$_3$)CH$_2$CH$_3$ |
| 99 | NHCH$_2$CH$_2$CH(CH$_3$)$_2$ |
| 100 | NHC(CH$_3$)$_2$CH$_2$CH$_3$ |
| 101 | NHCH$_2$C(CH$_3$)$_3$ |
| 102 | NHCH$_2$CH$_2$CH$_2$CH$_2$CH$_2$CH$_3$ |
| 103 | NHCH(CH$_3$)CH$_2$CH$_2$CH$_2$CH$_3$ |
| 104 | NHCH$_2$CH(CH$_3$)CH$_2$CH$_2$CH$_3$ |
| 105 | NHCH$_2$CH$_2$CH(CH$_3$)CH$_2$CH$_3$ |
| 106 | NHCH$_2$CH$_2$CH(CH$_3$)$_3$ |
| 107 | NHCH=CH$_2$ |

TABLE 1-continued

| | |
|---|---|
| 108 | $NHCH_2CH=CH_2$ |
| 109 | $NHC(CH_3)=CH_2$ |
| 110 | $NHCH=CHCH_3$ |
| 111 | $NHCH=CHCH_2CH_3$ |
| 112 | $NHCH_2CH=CHCH_3$ |
| 113 | $NHCH_2CH_2CH=CH_2$ |
| 114 | $NHCH=CHCH=CH_2$ |
| 115 | $NHCH_2C(CH_3)=CH_2$ |
| 116 | $NHPh$ |
| 117 | $NHCH_2Ph$ |
| 118 | $NHC_6H_4\text{-}2\text{-}CH_3$ |
| 119 | $NHC_6H_4\text{-}3\text{-}CH_3$ |
| 120 | $NHC_6H_4\text{-}4\text{-}CH_3$ |
| 121 | $NHC_6H_4\text{-}2,3\text{-}(CH_3)_2$ |
| 122 | $NHC_6H_4\text{-}2,4\text{-}(CH_3)_2$ |
| 123 | $NHC_6H_4\text{-}2,5\text{-}(CH_3)_2$ |
| 124 | $NHC_6H_4\text{-}2,6\text{-}(CH_3)_2$ |
| 125 | $NHC_6H_3\text{-}2,4,6\text{-}(CH_3)_3$ |
| 126 | $NHCH_2C_6H_4\text{-}2,3\text{-}(CH_3)_2$ |
| 127 | $NHCH_2C_6H_4\text{-}2,4\text{-}(CH_3)_2$ |
| 128 | $NHCH_2C_6H_4\text{-}2,5\text{-}(CH_3)_2$ |
| 129 | $NHCH_2C_6H_4\text{-}2,6\text{-}(CH_3)_2$ |
| 130 | $NHCH_2C_6H_3\text{-}2,4,6\text{-}(CH_3)_3$ |
| 131 | $N(CH_3)_2$ |
| 132 | $N(CH_2CH_3)_2$ |
| 133 | $N(CH_2CH_2CH_3)_2$ |
| 134 | $N(CH(CH_3)_2)_2$ |
| 135 | $N(CH_2CH_2CH_2CH_3)_2$ |
| 136 | $N(CH(CH_3)CH_2CH_3)_2$ |
| 137 | $N(CH_2CH(CH_3)_2)_2$ |
| 138 | $N(C(CH_3)_3)_2$ |
| 139 | $N(CH_2CH_2CH_2CH_2CH_3)_2$ |
| 140 | $N(CH(CH_3)CH_2CH_2CH_3)_2$ |
| 141 | $N(CH_2CH(CH_3)CH_2CH_3)_2$ |
| 142 | $N(CH_2CH_2CH(CH_3)_2)_2$ |
| 143 | $N(C(CH_3)_2CH_2CH_3)_2$ |
| 144 | $N(CH_2C(CH_3)_3)_2$ |
| 145 | $N(CH_2CH_2CH_2CH_2CH_2CH_3)_2$ |
| 146 | $N(CH(CH_3)CH_2CH_2CH_2CH_3)_2$ |
| 147 | $N(CH_2CH(CH_3)CH_2CH_2CH_3)_2$ |
| 148 | $N(CH_2CH_2CH(CH_3)CH_2CH_3)_2$ |
| 149 | $N(CH_2CH_2CH(CH_3)_3)_2$ |
| 150 | $N(CH=CH_2)_2$ |
| 151 | $N(CH_2CH=CH_2)_2$ |
| 152 | $N(C(CH_3)=CH_2)_2$ |
| 153 | $N(CH=CHCH_3)_2$ |
| 154 | $N(CH=CHCH_2CH_3)_2$ |
| 155 | $N(CH_2CH=CHCH_3)_2$ |
| 156 | $N(CH_2CH_2CH=CH_2)_2$ |
| 157 | $N(CH=CHCH=CH_2)_2$ |
| 158 | $N(CH_2C(CH_3)=CH_2)_2$ |
| 159 | $NPh_2$ |
| 160 | $N(CH_2Ph)_2$ |
| 161 | $N(C_6H_4\text{-}2\text{-}CH_3)_2$ |
| 162 | $N(C_6H_4\text{-}3\text{-}CH_3)_2$ |
| 163 | $N(C_6H_4\text{-}4\text{-}CH_3)_2$ |
| 164 | $N(C_6H_4\text{-}2,3\text{-}(CH_3)_2)_2$ |
| 165 | $N(C_6H_4\text{-}2,4\text{-}(CH_3)_2)_2$ |
| 166 | $N(C_6H_4\text{-}2,5\text{-}(CH_3)_2)_2$ |
| 167 | $N(C_6H_4\text{-}2,6\text{-}(CH_3)_2)_2$ |
| 168 | $N(C_6H_3\text{-}2,4,6\text{-}(CH_3)_3)_2$ |
| 169 | $N(CH_2C_6H_4\text{-}2,3\text{-}(CH_3)_2)_2$ |
| 170 | $N(CH_2C_6H_4\text{-}2,4\text{-}(CH_3)_2)_2$ |
| 171 | $N(CH_2C_6H_4\text{-}2,5\text{-}(CH_3)_2)_2$ |
| 172 | $N(CH_2C_6H_4\text{-}2,6\text{-}(CH_3)_2)_2$ |
| 173 | $N(CH_2C_6H_3\text{-}2,4,6\text{-}(CH_3)_3)_2$ |
| 174 | $N(CH_3)Ph$ |
| 175 | $N(CH_2CH_3)Ph$ |
| 176 | $N(CH_2CH_2CH_3)Ph$ |
| 177 | $N(CH_2(CH_2)_2CH_3)Ph$ |
| 178 | $N(CH(CH_3)CH_2CH_3)Ph$ |
| 179 | $N(CH_2CH(CH_3)_2)Ph$ |
| 180 | $N(C(CH_3)_3)Ph$ |
| 181 | $N(CH_2(CH_2)_3CH_3)Ph$ |
| 182 | $N(CH(CH_3)CH_2CH_2CH_3)Ph$ |
| 183 | $N(CH_2CH(CH_3)CH_2CH_3)Ph$ |
| 184 | $N(CH_2CH_2CH(CH_3)_2)Ph$ |
| 185 | $N(CH_2C(CH_3)_3)Ph$ |
| 186 | $N(CH_2(CH_2)_4CH_3)Ph$ |
| 187 | $N(CH(CH_3)(CH_2)_3CH_3)Ph$ |

TABLE 1-continued

| No. | |
|---|---|
| 188 | N(CH₂CH(CH₃)CH₂CH₂CH₃)Ph |
| 189 | N(CH₂CH₂CH(CH₃)CH₂CH₃)Ph |
| 190 | N(CH₂CH₂CH₂CH(CH₃)₂)Ph |
| 191 | N(CH₂CH₂C(CH₃)₃)Ph |
| 192 |  |
| 193 |  |
| 194 |  |
| 195 |  |
| 196 |  |
| 197 | 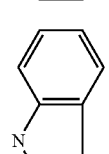 |
| 198 | ONa |
| 199 | OK |
| 200 | O—MgOH |
| 201 | O—CaOH |
| 202 | O—BaOH |
| 203 | O—MnOH |
| 204 | O—Fe or O—FeOH |
| 205 | O—ZnOH |

Table 1(2)

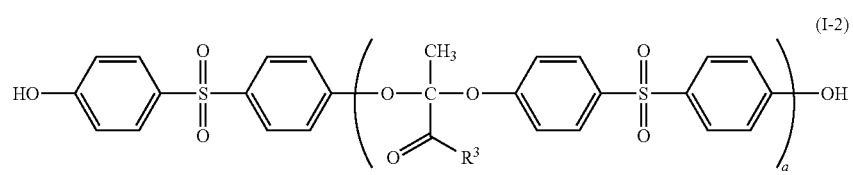

(I-2)

*a* represents an integer of 1 to 10.

| No. | R³ |
|---|---|
| 206 | OH |
| 207 | OCH₃ |
| 208 | OCH₂CH₃ |
| 209 | OCH₂CH₂CH₃ |
| 210 | OCH(CH₃)₂ |
| 211 | OCH₂CH₂CH₂CH₃ |
| 212 | OCH(CH₃)CH₂CH₃ |
| 213 | OCH₂CH(CH₃)₂ |
| 214 | OC(CH₃)₃ |
| 215 | OCH₂CH₂CH₂CH₂CH₃ |
| 216 | OCH(CH₃)CH₂CH₂CH₃ |
| 217 | OCH₂CH(CH₃)CH₂CH₃ |
| 218 | OCH₂CH₂CH(CH₃)₂ |
| 219 | OC(CH₃)₂CH₂CH₃ |
| 220 | OCH₂C(CH₃)₃ |
| 221 | OCH₂CH₂CH₂CH₂CH₂CH₃ |
| 222 | OCH(CH₃)CH₂CH₂CH₂CH₃ |
| 223 | OCH₂CH(CH₃)CH₂CH₂CH₃ |
| 224 | OCH₂CH₂CH(CH₃)CH₂CH₃ |

TABLE 1-continued

| | |
|---|---|
| 225 | OCH$_2$CH$_2$CH(CH$_3$)$_3$ |
| 226 | OCH=CH$_2$ |
| 227 | OCH$_2$CH=CH$_2$ |
| 228 | OC(CH$_3$)=CH$_2$ |
| 229 | OCH=CHCH$_3$ |
| 230 | OCH=CHCH$_2$CH$_3$ |
| 231 | OCH$_2$CH=CHCH$_3$ |
| 232 | OCH$_2$CH$_2$CH=CH$_2$ |
| 233 | OCH=CHCH=CH$_2$ |
| 234 | OCH$_2$C(CH$_3$)=CH$_2$ |
| 235 | OPh |
| 236 | OCH$_2$Ph |
| 237 | OC$_6$H$_4$-2-CH$_3$ |
| 238 | OC$_6$H$_4$-3-CH$_3$ |
| 239 | OC$_6$H$_4$-4-CH$_3$ |
| 240 | OC$_6$H$_4$-2,3-(CH$_3$)$_2$ |
| 241 | OC$_6$H$_4$-2,4-(CH$_3$)$_2$ |
| 242 | OC$_6$H$_4$-2,5-(CH$_3$)$_2$ |
| 243 | OC$_6$H$_4$-2,6-(CH$_3$)$_2$ |
| 244 | OC$_6$H$_3$-2,4,6-(CH$_3$)$_3$ |
| 245 | OCH$_2$C$_6$H$_4$-2,3-(CH$_3$)$_2$ |
| 246 | OCH$_2$C$_6$H$_4$-2,4-(CH$_3$)$_2$ |
| 247 | OCH$_2$C$_6$H$_4$-2,5-(CH$_3$)$_2$ |
| 248 | OCH$_2$C$_6$H$_4$-2,6-(CH$_3$)$_2$ |
| 249 | OCH$_2$C$_6$H$_3$-2,4,6-(CH$_3$)$_3$ |
| 250 | SCH$_3$ |
| 251 | SCH$_2$CH$_3$ |
| 252 | SCH$_2$CH$_2$CH$_3$ |
| 253 | SCH(CH$_3$)$_2$ |
| 254 | SCH$_2$CH$_2$CH$_2$CH$_3$ |
| 255 | SCH(CH$_3$)CH$_2$CH$_3$ |
| 256 | SCH$_2$CH(CH$_3$)$_2$ |
| 257 | SC(CH$_3$)$_3$ |
| 258 | SCH$_2$CH$_2$CH$_2$CH$_2$CH$_3$ |
| 259 | SCH(CH$_3$)CH$_2$CH$_2$CH$_3$ |
| 260 | SCH$_2$CH(CH$_3$)CH$_2$CH$_3$ |
| 261 | SCH$_2$CH$_2$CH(CH$_3$)$_2$ |
| 262 | SC(CH$_3$)$_2$CH$_2$CH$_3$ |
| 263 | SCH$_2$C(CH$_3$)$_3$ |
| 264 | SCH$_2$CH$_2$CH$_2$CH$_2$CH$_2$CH$_3$ |
| 265 | SCH(CH$_3$)CH$_2$CH$_2$CH$_2$CH$_3$ |
| 266 | SCH$_2$CH(CH$_3$)CH$_2$CH$_2$CH$_3$ |
| 267 | SCH$_2$CH$_2$CH(CH$_3$)CH$_2$CH$_3$ |
| 268 | SCH$_2$CH$_2$CH(CH$_3$)$_3$ |
| 269 | SCH=CH$_2$ |
| 270 | SCH$_2$CH=CH$_2$ |
| 271 | SC(CH$_3$)=CH$_2$ |
| 272 | SCH=CHCH$_3$ |
| 273 | SCH=CHCH$_2$CH$_3$ |
| 274 | SCH$_2$CH=CHCH$_3$ |
| 275 | SCH$_2$CH$_2$CH=CH$_2$ |
| 276 | SCH=CHCH=CH$_2$ |
| 277 | SCH$_2$C(CH$_3$)=CH$_2$ |
| 278 | SPh |
| 279 | SCH$_2$Ph |
| 280 | SC$_6$H$_4$-2-CH$_3$ |
| 281 | SC$_6$H$_4$-3-CH$_3$ |
| 282 | SC$_6$H$_4$-4-CH$_3$ |
| 283 | SC$_6$H$_4$-2,3-(CH$_3$)$_2$ |
| 284 | SC$_6$H$_4$-2,4-(CH$_3$)$_2$ |
| 285 | SC$_6$H$_4$-2,5-(CH$_3$)$_2$ |
| 286 | SC$_6$H$_4$-2,6-(CH$_3$)$_2$ |
| 287 | SC$_6$H$_3$-2,4,6-(CH$_3$)$_3$ |
| 288 | SCH$_2$C$_6$H$_4$-2,3-(CH$_3$)$_2$ |
| 289 | SCH$_2$C$_6$H$_4$-2,4-(CH$_3$)$_2$ |
| 290 | SCH$_2$C$_6$H$_4$-2,5-(CH$_3$)$_2$ |
| 291 | SCH$_2$C$_6$H$_4$-2,6-(CH$_3$)$_2$ |
| 292 | SCH$_2$C$_6$H$_3$-2,4,6-(CH$_3$)$_3$ |
| 293 | NHCH$_3$ |
| 294 | NHCH$_2$CH$_3$ |
| 295 | NHCH$_2$CH$_2$CH$_3$ |
| 296 | NHCH(CH$_3$)$_2$ |
| 297 | NHCH$_2$CH$_2$CH$_2$CH$_3$ |
| 298 | NHCH(CH$_3$)CH$_2$CH$_3$ |
| 299 | NHCH$_2$CH(CH$_3$)$_2$ |
| 300 | NHC(CH$_3$)$_3$ |
| 301 | NHCH$_2$CH$_2$CH$_2$CH$_2$CH$_3$ |
| 302 | NHCH(CH$_3$)CH$_2$CH$_2$CH$_3$ |
| 303 | NHCH$_2$CH(CH$_3$)CH$_2$CH$_3$ |
| 304 | NHCH$_2$CH$_2$CH(CH$_3$)$_2$ |

TABLE 1-continued

| | |
|---|---|
| 305 | NHC(CH$_3$)$_2$CH$_2$CH$_3$ |
| 306 | NHCH$_2$C(CH$_3$)$_3$ |
| 307 | NHCH$_2$CH$_2$CH$_2$CH$_2$CH$_2$CH$_3$ |
| 308 | NHCH(CH$_3$)CH$_2$CH$_2$CH$_2$CH$_3$ |
| 309 | NHCH$_2$CH(CH$_3$)CH$_2$CH$_2$CH$_3$ |
| 310 | NHCH$_2$CH$_2$CH(CH$_3$)CH$_2$CH$_3$ |
| 311 | NHCH$_2$CH$_2$CH(CH$_3$)$_3$ |
| 312 | NHCH=CH$_2$ |
| 313 | NHCH$_2$CH=CH$_2$ |
| 314 | NHC(CH$_3$)=CH$_2$ |
| 315 | NHCH=CHCH$_3$ |
| 316 | NHCH=CHCH$_2$CH$_3$ |
| 317 | NHCH$_2$CH=CHCH$_3$ |
| 318 | NHCH$_2$CH$_2$CH=CH$_2$ |
| 319 | NHCH=CHCH=CH$_2$ |
| 320 | NHCH$_2$C(CH$_3$)=CH$_2$ |
| 321 | NHPh |
| 322 | NHCH$_2$Ph |
| 323 | NHC$_6$H$_4$-2-CH$_3$ |
| 324 | NHC$_6$H$_4$-3-CH$_3$ |
| 325 | NHC$_6$H$_4$-4-CH$_3$ |
| 326 | NHC$_6$H$_4$-2,3-(CH$_3$)$_2$ |
| 327 | NHC$_6$H$_4$-2,4-(CH$_3$)$_2$ |
| 328 | NHC$_6$H$_4$-2,5-(CH$_3$)$_2$ |
| 329 | NHC$_6$H$_4$-2,6-(CH$_3$)$_2$ |
| 330 | NHC$_6$H$_3$-2,4,6-(CH$_3$)$_3$ |
| 331 | NHCH$_2$C$_6$H$_4$-2,3-(CH$_3$)$_2$ |
| 332 | NHCH$_2$C$_6$H$_4$-2,4-(CH$_3$)$_2$ |
| 333 | NHCH$_2$C$_6$H$_4$-2,5-(CH$_3$)$_2$ |
| 334 | NHCH$_2$C$_6$H$_4$-2,6-(CH$_3$)$_2$ |
| 335 | NHCH$_2$C$_6$H$_3$-2,4,6-(CH$_3$)$_3$ |
| 336 | N(CH$_3$)$_2$ |
| 337 | N(CH$_2$CH$_3$)$_2$ |
| 338 | N(CH$_2$CH$_2$CH$_3$)$_2$ |
| 339 | N(CH(CH$_3$)$_2$)$_2$ |
| 340 | N(CH$_2$CH$_2$CH$_2$CH$_3$)$_2$ |
| 341 | N(CH(CH$_3$)CH$_2$CH$_3$)$_2$ |
| 342 | N(CH$_2$CH(CH$_3$)$_2$)$_2$ |
| 343 | N(C(CH$_3$)$_3$)$_2$ |
| 344 | N(CH$_2$CH$_2$CH$_2$CH$_2$CH$_3$)$_2$ |
| 345 | N(CH(CH$_3$)CH$_2$CH$_2$CH$_3$)$_2$ |
| 346 | N(CH$_2$CH(CH$_3$)CH$_2$CH$_3$)$_2$ |
| 347 | N(CH$_2$CH$_2$CH(CH$_3$)$_2$)$_2$ |
| 348 | N(C(CH$_3$)$_2$CH$_2$CH$_3$)$_2$ |
| 349 | N(CH$_2$C(CH$_3$)$_3$)$_2$ |
| 350 | N(CH$_2$CH$_2$CH$_2$CH$_2$CH$_2$CH$_3$)$_2$ |
| 351 | N(CH(CH$_3$)CH$_2$CH$_2$CH$_2$CH$_3$)$_2$ |
| 352 | N(CH$_2$CH(CH$_3$)CH$_2$CH$_2$CH$_3$)$_2$ |
| 353 | N(CH$_2$CH$_2$CH(CH$_3$)CH$_2$CH$_3$)$_2$ |
| 354 | N(CH$_2$CH$_2$CH(CH$_3$)$_3$)$_2$ |
| 355 | N(CH=CH$_2$)$_2$ |
| 356 | N(CH$_2$CH=CH$_2$)$_2$ |
| 357 | N(C(CH$_3$)=CH$_2$)$_2$ |
| 358 | N(CH=CHCH$_2$)$_2$ |
| 359 | N(CH=CHCH$_2$CH$_3$)$_2$ |
| 360 | N(CH$_2$CH=CHCH$_3$)$_2$ |
| 361 | N(CH$_2$CH$_2$CH=CH$_2$)$_2$ |
| 362 | N(CH=CHCH=CH$_2$)$_2$ |
| 363 | N(CH$_2$C(CH$_3$)=CH$_2$)$_2$ |
| 364 | NPh$_2$ |
| 365 | N(CH$_2$Ph)$_2$ |
| 366 | N(C$_6$H$_4$-2-CH$_3$)$_2$ |
| 367 | N(C$_6$H$_4$-3-CH$_3$)$_2$ |
| 368 | N(C$_6$H$_4$-4-CH$_3$)$_2$ |
| 369 | N(C$_6$H$_4$-2,3-(CH$_3$)$_2$)$_2$ |
| 370 | N(C$_6$H$_4$-2,4-(CH$_3$)$_2$)$_2$ |
| 371 | N(C$_6$H$_4$-2,5-(CH$_3$)$_2$)$_2$ |
| 372 | N(C$_6$H$_4$-2,6-(CH$_3$)$_2$)$_2$ |
| 373 | N(C$_6$H$_3$-2,4,6-(CH$_3$)$_3$)$_2$ |
| 374 | N(CH$_2$C$_6$H$_4$-2,3-(CH$_3$)$_2$)$_2$ |
| 375 | N(CH$_2$C$_6$H$_4$-2,4-(CH$_3$)$_2$)$_2$ |
| 376 | N(CH$_2$C$_6$H$_4$-2,5-(CH$_3$)$_2$)$_2$ |
| 377 | N(CH$_2$C$_6$H$_4$-2,6-(CH$_3$)$_2$)$_2$ |
| 378 | N(CH$_2$C$_6$H$_3$-2,4,6-(CH$_3$)$_3$)$_2$ |
| 379 | N(CH$_3$)Ph |
| 380 | N(CH$_2$CH$_3$)Ph |
| 381 | N(CH$_2$CH$_2$CH$_3$)Ph |
| 382 | N(CH$_2$(CH$_2$)$_2$CH$_3$)Ph |
| 383 | N(CH(CH$_3$)CH$_2$CH$_3$)Ph |
| 384 | N(CH$_2$CH(CH$_3$)$_2$)Ph |

TABLE 1-continued

| | |
|---|---|
| 385 | N(C(CH₃)₃)Ph |
| 386 | N(CH₂(CH₂)₃CH₃)Ph |
| 387 | N(CH(CH₃)CH₂CH₂CH₃)Ph |
| 388 | N(CH₂CH(CH₃)CH₂CH₃)Ph |

[Table 10]

| | |
|---|---|
| 389 | N(CH₂CH₂CH(CH₃)₂)Ph |
| 390 | N(CH₂C(CH₃)₃)Ph |
| 391 | N(CH₂(CH₂)₄CH₃)Ph |
| 392 | N(CH(CH₃)(CH₂)₃CH)Ph |
| 393 | N(CH₂CH(CH₃)CH₂CH₂CH₃)Ph |
| 394 | N(CH₂CH₂CH(CH₃)CH₂CH₃)Ph |
| 395 | N(CH₂CH₂CH₂CH(CH₃)₂)Ph |
| 396 | N(CH₂CH₂C(CH₃)₃)Ph |
| 397 | piperidinyl |
| 398 | morpholinyl |
| 399 | thiomorpholinyl |
| 400 | pyrrolidinyl |
| 401 | pyrrolyl |
| 402 | indolyl |
| 403 | ONa |
| 404 | OK |
| 405 | O—MgOH |
| 406 | O—CaOH |
| 407 | O—BaOH |
| 408 | O—MnOH |
| 409 | O—Fe or O—FeOH |
| 410 | O—ZnOH |

Table 1(3)

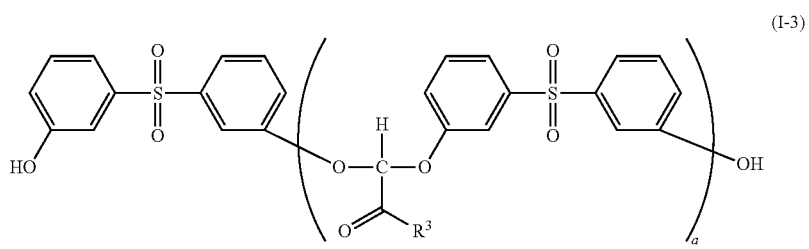

(I-3)

*a* represents an integer of 1 to 10.

| No. | R³ |
|---|---|
| 411 | OH |
| 412 | OCH₃ |
| 413 | OCH₂CH₃ |
| 414 | OCH₂CH₂CH₃ |

TABLE 1-continued

| | |
|---|---|
| 415 | OCH(CH$_3$)$_2$ |
| 416 | OCH$_2$CH$_2$CH$_2$CH$_3$ |
| 417 | OCH(CH$_3$)CH$_2$CH$_3$ |
| 418 | OCH$_2$CH(CH$_3$)$_2$ |
| 419 | OC(CH$_3$)$_3$ |
| 420 | OCH$_2$CH$_2$CH$_2$CH$_2$CH$_3$ |
| 421 | OCH(CH$_3$)CH$_2$CH$_2$CH$_3$ |
| 422 | OCH$_2$CH(CH$_3$)CH$_2$CH$_3$ |
| 423 | OCH$_2$CH$_2$CH(CH$_3$)$_2$ |
| 424 | OC(CH$_3$)$_2$CH$_2$CH$_3$ |
| 425 | OCH$_2$C(CH$_3$)$_3$ |
| 426 | OCH$_2$CH$_2$CH$_2$CH$_2$CH$_2$CH$_3$ |
| 427 | OCH(CH$_3$)CH$_2$CH$_2$CH$_2$CH$_3$ |
| 428 | OCH$_2$CH(CH$_3$)CH$_2$CH$_2$CH$_3$ |
| 429 | OCH$_2$CH$_2$CH(CH$_3$)CH$_2$CH$_3$ |
| 430 | OCH$_2$CH$_2$CH(CH$_3$)$_3$ |
| 431 | OCH=CH$_2$ |
| 432 | OCH$_2$CH=CH$_2$ |
| 433 | OC(CH$_3$)=CH$_2$ |
| 434 | OCH=CHCH$_3$ |
| 435 | OCH=CHCH$_2$CH$_3$ |
| 436 | OCH$_2$CH=CHCH$_3$ |
| 437 | OCH$_2$CH$_2$CH=CH$_2$ |
| 438 | OCH=CHCH=CH$_2$ |
| 439 | OCH$_2$C(CH$_3$)=CH$_2$ |
| 440 | OPh |
| 441 | OCH$_2$Ph |
| 442 | OC$_6$H$_4$-2-CH$_3$ |
| 443 | OC$_6$H$_4$-3-CH$_3$ |
| 444 | OC$_6$H$_4$-4-CH$_3$ |
| 445 | OC$_6$H$_4$-2,3-(CH$_3$)$_2$ |
| 446 | OC$_6$H$_4$-2,4-(CH$_3$)$_2$ |
| 447 | OC$_6$H$_4$-2,5-(CH$_3$)$_2$ |
| 448 | OC$_6$H$_4$-2,6-(CH$_3$)$_2$ |
| 449 | OC$_6$H$_3$-2,4,6-(CH$_3$)$_3$ |
| 450 | OCH$_2$C$_6$H$_4$-2,3-(CH$_3$)$_2$ |
| 451 | OCH$_2$C$_6$H$_4$-2,4-(CH$_3$)$_2$ |
| 452 | OCH$_2$C$_6$H$_4$-2,5-(CH$_3$)$_2$ |
| 453 | OCH$_2$C$_6$H$_4$-2,6-(CH$_3$)$_2$ |
| 454 | OCH$_2$C$_6$H$_3$-2,4,6-(CH$_3$)$_3$ |
| 455 | SCH$_3$ |
| 456 | SCH$_2$CH$_3$ |
| 457 | SCH$_2$CH$_2$CH$_3$ |
| 458 | SCH(CH$_3$)$_2$ |
| 459 | SCH$_2$CH$_2$CH$_2$CH$_3$ |
| 460 | SCH(CH$_3$)CH$_2$CH$_3$ |
| 461 | SCH$_2$CH(CH$_3$)$_2$ |
| 462 | SC(CH$_3$)$_3$ |
| 463 | SCH$_2$CH$_2$CH$_2$CH$_2$CH$_3$ |
| 464 | SCH(CH$_3$)CH$_2$CH$_2$CH$_3$ |
| 465 | SCH$_2$CH(CH$_3$)CH$_2$CH$_3$ |
| 466 | SCH$_2$CH$_2$CH(CH$_3$)$_2$ |
| 467 | SC(CH$_3$)$_2$CH$_2$CH$_3$ |
| 468 | SCH$_2$C(CH$_3$)$_3$ |
| 469 | SCH$_2$CH$_2$CH$_2$CH$_2$CH$_2$CH$_3$ |
| 470 | SCH(CH$_3$)CH$_2$CH$_2$CH$_2$CH$_3$ |
| 471 | SCH$_2$CH(CH$_3$)CH$_2$CH$_2$CH$_3$ |
| 472 | SCH$_2$CH$_2$CH(CH$_3$)CH$_2$CH$_3$ |
| 473 | SCH$_2$CH$_2$CH(CH$_3$)$_3$ |
| 474 | SCH=CH$_2$ |
| 475 | SCH$_2$CH=CH$_2$ |
| 476 | SC(CH$_3$)=CH$_2$ |
| 477 | SCH=CHCH$_3$ |
| 478 | SCH=CHCH$_2$CH$_3$ |
| 479 | SCH$_2$CH=CHCH$_3$ |
| 480 | SCH$_2$CH$_2$CH=CH$_2$ |
| 481 | SCH=CHCH=CH$_2$ |
| 482 | SCH$_2$C(CH$_3$)=CH$_2$ |
| 483 | SPh |
| 484 | SCH$_2$Ph |
| 485 | SC$_6$H$_4$-2-CH$_3$ |
| 486 | SC$_6$H$_4$-3-CH$_3$ |
| 487 | SC$_6$H$_4$-4-CH$_3$ |
| 488 | SC$_6$H$_4$-2,3-(CH$_3$)$_2$ |
| 489 | SC$_6$H$_4$-2,4-(CH$_3$)$_2$ |
| 490 | SC$_6$H$_4$-2,5-(CH$_3$)$_2$ |
| 491 | SC$_6$H$_4$-2,6-(CH$_3$)$_2$ |
| 492 | SC$_6$H$_3$-2,4,6-(CH$_3$)$_3$ |
| 493 | SCH$_2$C$_6$H$_4$-2,3-(CH$_3$)$_2$ |
| 494 | SCH$_2$C$_6$H$_4$-2,4-(CH$_3$)$_2$ |

TABLE 1-continued

| | |
|---|---|
| 495 | $SCH_2C_6H_4$-2,5-$(CH_3)_2$ |
| 496 | $SCH_2C_6H_4$-2,6-$(CH_3)_2$ |
| 497 | $SCH_2C_6H_3$-2,4,6-$(CH_3)_3$ |
| 498 | $NHCH_3$ |
| 499 | $NHCH_2CH_3$ |
| 500 | $NHCH_3CH_2CH_3$ |
| 501 | $NHCH(CH_3)_2$ |
| 502 | $NHCH_2CH_2CH_3$ |
| 503 | $NHCH(CH_3)CH_2CH_3$ |
| 504 | $NHCH_2CH(CH_3)_2$ |
| 505 | $NHC(CH_3)_3$ |
| 506 | $NHCH_2CH_2CH_2CH_2CH_3$ |
| 507 | $NHCH(CH_3)CH_2CH_2CH_3$ |
| 508 | $NHCH_2CH(CH_3)CH_2CH_3$ |
| 509 | $NHCH_2CH_2CH(CH_3)_2$ |
| 510 | $NHC(CH_3)_2CH_2CH_3$ |
| 511 | $NHCH_2C(CH_3)_3$ |
| 512 | $NHCH_2CH_2CH_2CH_2CH_2CH_3$ |
| 513 | $NHCH(CH_3)CH_2CH_2CH_2CH_3$ |
| 514 | $NHCH_2CH(CH_3)CH_2CH_2CH_3$ |
| 515 | $NHCH_2CH_2CH(CH_3)CH_2CH_3$ |
| 516 | $NHCH_2CH_2CH(CH_3)_3$ |
| 517 | $NHCH=CH_2$ |
| 518 | $NHCH_2CH=CH_2$ |
| 519 | $NHC(CH_3)=CH_2$ |
| 520 | $NHCH=CHCH_3$ |
| 521 | $NHCH=CHCH_2CH_3$ |
| 522 | $NHCH_2CH=CHCH_3$ |
| 523 | $NHCH_2CH_2CH=CH_2$ |
| 524 | $NHCH=CHCH=CH_2$ |
| 525 | $NHCH_2C(CH_3)=CH_2$ |
| 526 | $NHPh$ |
| 527 | $NHCH_2Ph$ |
| 528 | $NHC_6H_4$-2-$CH_3$ |
| 529 | $NHC_6H_4$-3-$CH_3$ |
| 530 | $NHC_6H_4$-4-$CH_3$ |
| 531 | $NHC_6H_4$-2,3-$(CH_3)_2$ |
| 532 | $NHC_6H_4$-2,4-$(CH_3)_2$ |
| 533 | $NHC_6H_4$-2,5-$(CH_3)_2$ |
| 534 | $NHC_6H_4$-2,6-$(CH_3)_2$ |
| 535 | $NHC_6H_3$-2,4,6-$(CH_3)_3$ |
| 536 | $NHCH_2C_6H_4$-2,3-$(CH_3)_2$ |
| 537 | $NHCH_2C_6H_4$-2,4-$(CH_3)_2$ |
| 538 | $NHCH_2C_6H_4$-2,5-$(CH_3)_2$ |
| 539 | $NHCH_2C_6H_4$-2,6-$(CH_3)_2$ |
| 540 | $NHCH_2C_6H_3$-2,4,6-$(CH_3)_3$ |
| 541 | $N(CH_3)_2$ |
| 542 | $N(CH_2CH_3)_2$ |
| 543 | $N(CH_2CH_2CH_3)_2$ |
| 544 | $N(CH(CH_3)_2)_2$ |
| 545 | $N(CH_2CH_2CH_2CH_3)_2$ |
| 546 | $N(CH(CH_3)CH_2CH_3)_2$ |
| 547 | $N(CH_2CH(CH_3)_2)_2$ |
| 548 | $N(C(CH_3)_3)_2$ |
| 549 | $N(CH_2CH_2CH_2CH_2CH_3)_2$ |
| 550 | $N(CH(CH_3)CH_2CH_2CH_3)_2$ |
| 551 | $N(CH_2CH(CH_3)CH_2CH_3)_2$ |
| 552 | $N(CH_2CH_2CH(CH_3)_2)_2$ |
| 553 | $N(C(CH_3)_2CH_2CH_3)_2$ |
| 554 | $N(CH_2C(CH_3)_3)_2$ |
| 555 | $N(CH_2CH_2CH_2CH_2CH_2CH_3)_2$ |
| 556 | $N(CH(CH_3)CH_2CH_2CH_2CH_3)_2$ |
| 557 | $N(CH_2CH(CH_3)CH_2CH_2CH_3)_2$ |
| 558 | $N(CH_2CH_2CH(CH_3)CH_2CH_3)_2$ |
| 559 | $N(CH_2CH_2CH(CH_3)_2)_2$ |
| 560 | $N(CH=CH_2)_2$ |
| 561 | $N(CH_2CH=CH_2)_2$ |
| 562 | $N(C(CH_3)=CH_2)_2$ |
| 563 | $N(CH=CHCH_3)_2$ |
| 564 | $N(CH=CHCH_2CH_3)_2$ |
| 565 | $N(CH_2CH=CHCH_3)_2$ |
| 566 | $N(CH_2CH_2CH=CH_2)_2$ |
| 567 | $N(CH=CHCH=CH_2)_2$ |
| 568 | $N(CH_2C(CH_3)=CH_2)_2$ |
| 569 | $NPh_2$ |
| 570 | $N(CH_2Ph)_2$ |
| 571 | $N(C_6H_4$-2-$CH_3)_2$ |
| 572 | $N(C_6H_4$-3-$CH_3)_2$ |
| 573 | $N(C_6H_4$-4-$CH_3)_2$ |
| 574 | $N(C_6H_4$-2,3-$(CH_3)_2)_2$ |

TABLE 1-continued

| | |
|---|---|
| 575 | N(C$_6$H$_4$-2,4-(CH$_3$)$_2$)$_2$ |
| 576 | N(C$_6$H4-2,5-(CH$_3$)$_2$)$_2$ |
| 577 | N(C$_6$H$_4$-2,6-(CH$_3$)$_2$)$_2$ |
| 578 | N(C$_6$H$_3$-2,4,6-(CH$_3$)$_3$)$_2$ |
| 579 | N(CH$_2$C$_6$H$_4$-2,3-(CH$_3$)$_2$)$_2$ |
| 580 | N(CH$_2$C$_6$H$_4$-2,4-(CH$_3$)$_2$)$_2$ |
| 581 | N(CH$_2$C$_6$H$_4$-2,5-(CH$_3$)$_2$)$_2$ |
| 582 | N(CH$_2$C$_6$H$_4$-2,6-(CH$_3$)$_2$)$_2$ |
| 583 | N(CH$_2$C$_6$H$_3$-2,4,6-(CH$_3$)$_3$)$_2$ |
| 584 | N(CH$_3$)Ph |
| 585 | N(CH$_2$CH$_3$)Ph |
| 586 | N(CH$_2$CH$_2$CH$_3$)Ph |
| 587 | N(CH$_2$(CH$_2$)$_2$CH$_3$)Ph |
| 588 | N(CH(CH$_3$)CH$_2$CH$_3$)Ph |
| 589 | N(CH$_2$CH(CH$_3$)$_2$)Ph |
| 590 | N(C(CH$_3$)$_3$)Ph |
| 591 | N(CH$_2$(CH$_2$)$_3$CH$_3$)Ph |
| 592 | N(CH(CH$_3$)CH$_2$CH$_2$CH$_3$)Ph |
| 593 | N(CH$_2$CH(CH$_3$)CH$_2$CH$_3$)Ph |
| 594 | N(CH$_2$CH$_2$CH(CH$_3$)$_2$)Ph |
| 595 | N(CH$_2$C(CH$_3$)$_3$)Ph |
| 596 | N(CH$_2$(CH$_2$)$_4$CH$_3$)Ph |
| 597 | N(CH(CH$_3$)(CH$_2$)$_3$CH$_3$)Ph |
| 598 | N(CH$_2$CH(CH$_3$)CH$_2$CH$_2$CH$_3$)Ph |
| 599 | N(CH$_2$CH$_2$CH(CH$_3$)CH$_2$CH$_3$)Ph |
| 600 | N(CH$_2$CH$_2$CH$_2$CH(CH$_3$)$_2$)Ph |
| 601 | N(CH$_2$CH$_2$C(CH$_3$)$_3$)Ph |
| 602 |  |
| 603 |  |
| 604 |  |
| 605 |  |
| 606 |  |
| 607 | 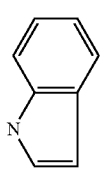 |
| 608 | ONa |
| 609 | OK |
| 610 | O—MgOH |
| 611 | O—CaOH |
| 612 | O—BaOH |
| 613 | O—MnOH |
| 614 | O—Fe or O—FeOH |
| 615 | O—ZnOH |

TABLE 1-continued

Table 1(4)

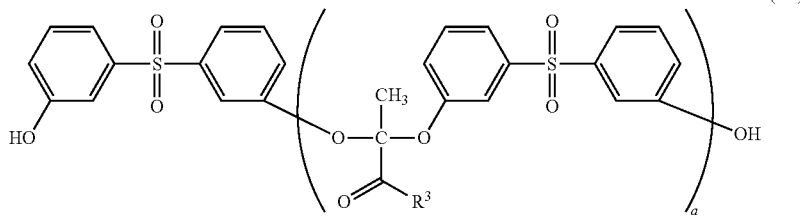

(I-4)

*a* represents an integer of 1 to 10.

| No. | R³ |
|-----|-----|
| 616 | OH |
| 617 | OCH₃ |
| 618 | OCH₂CH₃ |
| 619 | OCH₂CH₂CH₃ |
| 620 | OCH(CH₃)₂ |
| 621 | OCH₂CH₂CH₂CH₃ |
| 622 | OCH(CH₃)CH₂CH₃ |
| 623 | OCH₂CH(CH₃)₂ |
| 624 | OC(CH₃)₃ |
| 625 | OCH₂CH₂CH₂CH₂CH₃ |
| 626 | OCH(CH₃)CH₂CH₂CH₃ |
| 627 | OCH₂CH(CH₃)CH₂CH₃ |
| 628 | OCH₂CH₂CH(CH₃)₂ |
| 629 | OC(CH₃)₂CH₂CH₃ |
| 630 | OCH₂C(CH₃)₃ |
| 631 | OCH₂CH₂CH₂CH₂CH₂CH₃ |
| 632 | OCH(CH₃)CH₂CH₂CH₂CH₃ |
| 633 | OCH₂CH(CH₃)CH₂CH₂CH₃ |
| 634 | OCH₂CH₂CH(CH₃)CH₂CH₃ |
| 635 | OCH₂CH₂CH(CH₃)₃ |
| 636 | OCH=CH₂ |
| 637 | OCH₂CH=CH₂ |
| 638 | OC(CH₃)=CH₂ |
| 639 | OCH=CHCH₃ |
| 640 | OCH=CHCH₂CH₃ |
| 641 | OCH₂CH=CHCH₃ |
| 642 | OCHCH₂CH=CH₂ |
| 643 | OCH=CHCH=CH₂ |
| 644 | OCH₂C(CH₃)=CH₂ |
| 645 | OPh |
| 646 | OCH₂Ph |
| 647 | OC₆H₄-2-CH₃ |
| 648 | OC₆H₄-3-CH₃ |
| 649 | OC₆H₄-4-CH₃ |
| 650 | OC₆H₄-2,3-(CH₃)₂ |
| 651 | OC₆H₄-2,4-(CH₃)₂ |
| 652 | OC₆H₄-2,5-(CH₃)₂ |
| 653 | OC₆H₄-2,6-(CH₃)₂ |
| 654 | OC₆H₃-2,4,6-(CH₃)₃ |
| 655 | OCH₂C₆H₄-2,3-(CH₃)₂ |
| 656 | OCH₂C₆H₄-2,4-(CH₃)₂ |
| 657 | OCH₂C₆H₄-2,5-(CH₃)₂ |
| 658 | OCH₂C₆H₄-2,6-(CH₃)₂ |
| 659 | OCH₂C₆H₃-2,4,6-(CH₃)₃ |
| 660 | SCH₃ |
| 661 | SCH₂CH₃ |
| 662 | SCH₂CH₂CH₃ |
| 663 | SCH(CH₃)₂ |
| 664 | SCH₂CH₂CH₂CH₃ |
| 665 | SCH(CH₃)CH₂CH₃ |
| 666 | SCH₂CH(CH₃)₂ |
| 667 | SC(CH₃)₃ |
| 668 | SCH₂CH₂CH₂CH₂CH₃ |
| 669 | SCH(CH₃)CH₂CH₂CH₃ |
| 670 | SCH₂CH(CH₃)CH₂CH₃ |
| 671 | SCH₂CH₂CH(CH₃)₂ |
| 672 | SC(CH₃)₂CH₂CH₃ |
| 673 | SCH₂C(CH₃)₃ |
| 674 | SCH₂CH₂CH₂CH₂CH₂CH₃ |
| 675 | SCH(CH₃)CH₂CH₂CH₂CH₃ |
| 676 | SCH₂CH(CH₃)CH₂CH₂CH₃ |
| 677 | SCH₂CH₂CH(CH₃)CH₂CH₃ |

TABLE 1-continued

| | |
|---|---|
| 678 | SCH$_2$CH$_2$CH(CH$_3$)$_3$ |
| 679 | SCH=CH$_2$ |
| 680 | SCH$_2$CH=CH$_2$ |
| 681 | SC(CH$_3$)=CH$_2$ |
| 682 | SCH=CHCH$_3$ |
| 683 | SCH=CHCH$_2$CH$_3$ |
| 684 | SCH$_2$CH=CHCH$_3$ |
| 685 | SCH$_2$CH$_2$CH=CH$_2$ |
| 686 | SCH=CHCH=CH$_2$ |
| 687 | SCH$_2$C(CH$_3$)=CH$_2$ |
| 688 | SPh |
| 689 | SCH$_2$Ph |
| 690 | SC$_6$H$_4$-2-CH$_3$ |
| 691 | SC$_6$H$_4$-3-CH$_3$ |
| 692 | SC$_6$H$_4$-4-CH$_3$ |
| 693 | SC$_6$H$_4$-2,3-(CH$_3$)$_2$ |
| 694 | SC$_6$H$_4$-2,4-(CH$_3$)$_2$ |
| 695 | SC$_6$H$_4$-2,5-(CH$_3$)$_2$ |
| 696 | SC$_6$H$_4$-2,6-(CH$_3$)$_2$ |
| 697 | SC$_6$H$_3$-2,4,6-(CH$_3$)$_3$ |
| 698 | SCH$_2$C$_6$H$_4$-2,3-(CH$_3$)$_2$ |
| 699 | SCH$_2$C$_6$H$_4$-2,4-(CH$_3$)$_2$ |
| 700 | SCH$_2$C$_6$H$_4$-2,5-(CH$_3$)$_2$ |
| 701 | SCH$_2$C$_6$H$_4$-2,6-(CH$_3$)$_2$ |
| 702 | SCH$_2$C$_6$H$_3$-2,4,6-(CH$_3$)$_3$ |
| 703 | NHCH$_3$ |
| 704 | NHCH$_2$CH$_3$ |
| 705 | NHCH$_2$CH$_2$CH$_3$ |
| 706 | NHCH(CH$_3$)$_2$ |
| 707 | NHCH$_2$CH$_2$CH$_2$CH$_3$ |
| 708 | NHCH(CH$_3$)CH$_2$CH$_3$ |
| 709 | NHCH$_2$CH(CH$_3$)$_2$ |
| 710 | NHC(CH$_3$)$_3$ |
| 711 | NHCH$_2$CH$_2$CH$_2$CH$_2$CH$_3$ |
| 712 | NHCH(CH$_3$)CH$_2$CH$_2$CH$_3$ |
| 713 | NHCH$_2$CH(CH$_3$)CH$_2$CH$_3$ |
| 714 | NHCH$_2$CH$_2$CH(CH$_3$)$_2$ |
| 715 | NHC(CH$_3$)$_2$CH$_2$CH$_3$ |
| 716 | NHCH$_2$C(CH$_3$)$_3$ |
| 717 | NHCH$_2$CH$_2$CH$_2$CH$_2$CH$_2$CH$_3$ |
| 718 | NHCH(CH$_3$)CH$_2$CH$_2$CH$_2$CH$_3$ |
| 719 | NHCH$_2$CH(CH$_3$)CH$_2$CH$_2$CH$_3$ |
| 720 | NHCH$_2$CH$_2$CH(CH$_3$)CH$_2$CH$_3$ |
| 721 | NHCH$_2$CH$_2$CH(CH$_3$)$_3$ |
| 722 | NHCH=CH$_2$ |
| 723 | NHCH$_2$CH=CH$_2$ |
| 724 | NHC(CH$_3$)=CH$_2$ |
| 725 | NHCH=CHCH$_3$ |
| 726 | NHCH=CHCH$_2$CH$_3$ |
| 727 | NHCH$_2$CH=CHCH$_3$ |
| 728 | NHCH$_2$CH$_2$CH=CH$_2$ |
| 729 | NHCH=CHCH=CH$_2$ |
| 730 | NHCH$_2$C(CH$_3$)=CH$_2$ |
| 731 | NHPh |
| 732 | NHCH$_2$Ph |
| 733 | NHC$_6$H$_4$-2-CH$_3$ |
| 734 | NHC$_6$H$_4$-3-CH$_3$ |
| 735 | NHC$_6$H$_4$-4-CH$_3$ |
| 736 | NHC$_6$H$_4$-2,3-(CH$_3$)$_2$ |
| 737 | NHC$_6$H$_4$-2,4-(CH$_3$)$_2$ |
| 738 | NHC$_6$H$_4$-2,5-(CH$_3$)$_2$ |
| 739 | NHC$_6$H$_4$-2,6-(CH$_3$)$_2$ |
| 740 | NHC$_6$H$_3$-2,4,6-(CH$_3$)$_3$ |
| 741 | NHCH$_2$C$_6$H$_4$-2,3-(CH$_3$)$_2$ |
| 742 | NHCH$_2$C$_6$H$_4$-2,4-(CH$_3$)$_2$ |
| 743 | NHCH$_2$C$_6$H$_4$-2,5-(CH$_3$)$_2$ |
| 744 | NHCH$_2$C$_6$H$_4$-2,6-(CH$_3$)$_2$ |
| 745 | NHCH$_2$C$_6$H$_3$-2,4,6-(CH$_3$)$_3$ |
| 746 | N(CH$_3$)$_2$ |
| 747 | N(CH$_2$CH$_3$)$_2$ |
| 748 | N(CH$_2$CH$_2$CH$_3$)$_2$ |
| 749 | N(CH(CH$_3$)$_2$)$_2$ |
| 750 | N(CH$_2$CH$_2$CH$_2$CH$_3$)$_2$ |
| 751 | N(CH(CH$_3$)CH$_2$CH$_3$)$_2$ |
| 752 | N(CH$_2$CH(CH$_3$)$_2$)$_2$ |
| 753 | N(C(CH$_3$)$_3$)$_2$ |
| 754 | N(CH$_2$CH$_2$CH$_2$CH$_2$CH$_3$)$_2$ |
| 755 | N(CH(CH$_3$)CH$_2$CH$_2$CH$_3$)$_2$ |
| 756 | N(CH$_2$CH(CH$_3$)CH$_2$CH$_3$)$_2$ |
| 757 | N(CH$_2$CH$_2$CH(CH$_3$)$_2$)$_2$ |

TABLE 1-continued

| | |
|---|---|
| 758 | N(C(CH$_3$)$_2$CH$_2$CH$_3$)$_2$ |
| 759 | N(CH$_2$C(CH$_3$)$_3$)$_2$ |
| 760 | N(CH$_2$CH$_2$CH$_2$CH$_2$CH$_2$CH$_3$)$_2$ |
| 761 | N(CH(CH$_3$)CH$_2$CH$_2$CH$_2$CH$_3$)$_2$ |
| 762 | N(CH$_2$CH(CH$_3$)CH$_2$CH$_2$CH$_3$)$_2$ |
| 763 | N(CH$_2$CH$_2$CH(CH$_3$)CH$_2$CH$_3$)$_2$ |
| 764 | N(CH$_2$CH$_2$CH(CH$_3$)$_3$)$_2$ |
| 765 | N(CH=CH$_2$)$_2$ |
| 766 | N(CH$_2$CH=CH$_2$)$_2$ |
| 767 | N(C(CH$_3$)=CH$_2$)$_2$ |
| 768 | N(CH=CHCH$_3$)$_2$ |
| 769 | N(CH=CHCH$_2$CH$_3$)$_2$ |
| 770 | N(CH$_2$CH=CHCH$_3$)$_2$ |
| 771 | N(CH$_2$CH$_2$CH=CH$_2$)$_2$ |
| 772 | N(CH=CHCH=CH$_2$)$_2$ |
| 773 | N(CH$_2$C(CH$_3$)=CH$_2$)$_2$ |
| 774 | NPh$_2$ |
| 775 | N(CH$_2$Ph)$_2$ |
| 776 | N(C$_6$H$_4$-2-CH$_3$)$_2$ |
| 777 | N(C$_6$H$_4$-3-CH$_3$)$_2$ |
| 778 | N(C$_6$H$_4$-4-CH$_3$)$_2$ |
| 779 | N(C$_6$H$_4$-2,3-(CH$_3$)$_2$)$_2$ |
| 780 | N(C$_6$H$_4$-2,4-(CH$_3$)$_2$)$_2$ |
| 781 | N(C$_6$H$_4$-2,5-(CH$_3$)$_2$)$_2$ |
| 782 | N(C$_6$H$_4$-2,6-(CH$_3$)$_2$)$_2$ |
| 783 | N(C$_6$H$_3$-2,4,6-(CH$_3$)$_3$)$_2$ |
| 784 | N(CH$_2$C$_6$H$_4$-2,3-(CH$_3$)$_2$)$_2$ |
| 785 | N(CH$_2$C$_6$H$_4$-2,4-(CH$_3$)$_2$)$_2$ |
| 786 | N(CH$_2$C$_6$H$_4$-2,5-(CH$_3$)$_2$)$_2$ |
| 787 | N(CH$_2$C$_6$H$_4$-2,6-(CH$_3$)$_2$)$_2$ |
| 788 | N(CH$_2$C$_6$H$_3$-2,4,6-(CH$_3$)$_3$)$_2$ |
| 789 | N(CH$_3$)Ph |
| 790 | N(CH$_2$CH$_3$)Ph |
| 791 | N(CH$_2$CH$_2$CH$_3$)Ph |
| 792 | N(CH$_2$(CH$_2$)$_2$CH$_3$)Ph |
| 793 | N(CH(CH$_3$)CH$_2$CH$_3$)Ph |
| 794 | N(CH$_2$CH(CH$_3$)$_2$)Ph |
| 795 | N(C(CH$_3$)$_3$)Ph |
| 796 | N(CH$_2$(CH$_2$)$_3$CH$_3$)Ph |
| 797 | N(CH(CH$_3$)CH$_2$CH$_2$CH$_3$)Ph |
| 798 | N(CH$_2$CH(CH$_3$)CH$_2$CH$_3$)Ph |
| 799 | N(CH$_2$CH$_2$CH(CH$_3$)$_2$)Ph |
| 800 | N(CH$_2$C(CH$_3$)$_3$)Ph |
| 801 | N(CH$_2$(CH$_2$)$_4$CH$_3$)Ph |
| 802 | N(CH(CH$_3$)(CH$_2$)$_3$CH$_3$)Ph |
| 803 | N(CH$_2$CH(CH$_3$)CH$_2$CH$_2$CH$_3$)Ph |
| 804 | N(CH$_2$CH$_2$CH(CH$_3$)CH$_2$CH$_3$)Ph |
| 805 | N(CH$_2$CH$_2$CH$_2$CH(CH$_3$)$_2$)Ph |
| 806 | N(CH$_2$CH$_2$C(CH$_3$)$_3$)Ph |
| 807 |  |
| 808 |  |
| 809 |  |
| 810 |  |
| 811 |  |

TABLE 1-continued

| | |
|---|---|
| 812 | 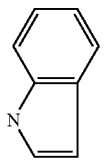 |
| 813 | ONa |
| 814 | OK |
| 815 | O—MgOH |
| 816 | O—CaOH |
| 817 | O—BaOH |
| 818 | O—MnOH |
| 819 | O—Fe or O—FeOH |
| 820 | O—ZnOH |

The compound of the present invention represented by the formula (I) has a repeat unit represented by the following formula:

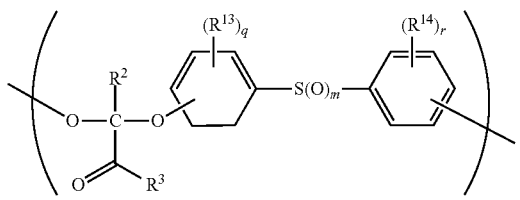

(wherein $R^2$, $R^3$, $R^{13}$, $R^{14}$, m, q, and r are as defined in the formula (I)).

When a represents 2 or more, the repeat units may not be the same as each other. Moreover, the number of the repeat unit is preferably between 2 and 10 inclusive.

The present invention also provides a mixture of compounds differing in the number a of repeat units. Specifically, the mixture may be a composition comprising a compound whose number a of repeat units is 1 and a compound whose number a of repeat units is 2 or more. The production ratios of the compounds differing in the number of repeat units differ depending on reaction conditions. The individual compounds can be isolated by recrystallization, column separation, and GPC-based fractionation methods. To obtain a composition containing a plurality of compounds differing in the number of repeat units, the isolated individual components may be mixed with each other, or a mixture obtained by reaction may be used directly.

(Method for Producing Compound Represented by the Formula (I))

The compound represented by the formula (I) may be produced by a production method known in the art. For example, a compound represented by the formula (I) wherein $R^{42}$ represents a hydrogen atom can be produced by the following production method:

A compound represented by the formula (III'):

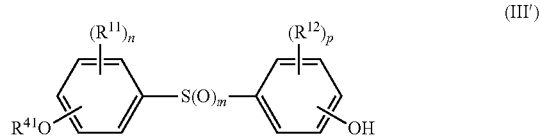

(wherein $R^{11}$, $R^{12}$, $R^{41}$, m, n, and p are as defined in the formula (I))

is reacted with a compound represented by the formula (IV):

$$X_2CR^2COR^3 \qquad (IV)$$

(wherein $R^2$ and $R^3$ are as defined in the formula (I); and each X independently represents a halogen atom)

under alkaline conditions to produce a compound represented by the formula (IX):

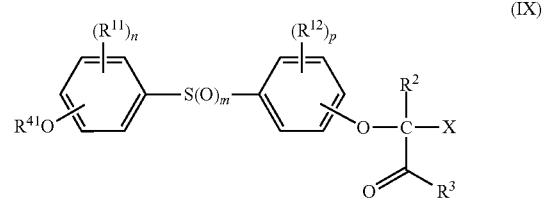

(wherein $R^2$, $R^3$, $R^{11}$, $R^{12}$, $R^{41}$, m, n, and p are as defined in the formula (I); and X is as defined in the formula (IV)). Next, the compound represented by the formula (IX) is reacted with a compound represented by the formula (III"):

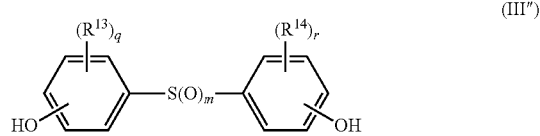

(wherein $R^{13}$, $R^{14}$, m, q, and r are as defined in the formula (I)) under alkaline conditions to produce a compound represented by the formula (X'):

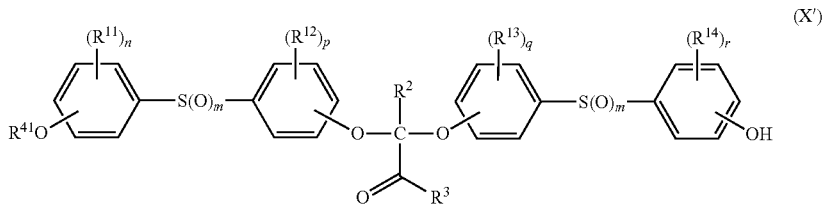

(wherein $R^2$, $R^3$, $R^{11}$, $R^{12}$, $R^{13}$, $R^{14}$, $R^{41}$, m, n, p, q, and r are as defined in the formula (I)). Then, the compound represented by the formula (IV) and the compound represented by the formula (III') can be added thereto at necessary number of moles and reacted under alkaline conditions to produce a compound represented by the formula (I') wherein a represents 2 or more:

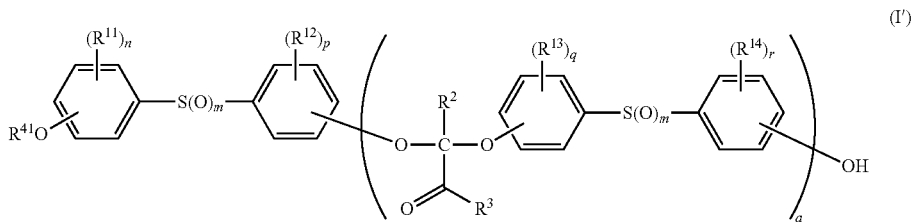

(wherein $R^2$, $R^3$, $R^{11}$, $R^{12}$, $R^{13}$, $R^{14}$, $R^{41}$, m, n, p, q, and r are as defined in the formula (I)).

A compound represented by the formula (I) wherein $R^{42}$ represents a group other than a hydrogen atom can be produced by further reacting the compound represented by the formula (I') with a halide represented by the following formula:

$$R^{42}X$$

(wherein X represents a halogen atom; and $R^{42}$ represents a $C_1$-$C_6$ alkyl group, a $C_2$-$C_6$ alkenyl group, or a protective group for the hydroxy group).

In the reactions described above, a compound that creates the alkaline conditions is not limited, and both inorganic and organic compounds may be used. An appropriate compound is used according to a solvent used. Examples thereof can specifically include: inorganic compounds such as sodium hydroxide, potassium hydroxide, calcium hydroxide, barium hydroxide, sodium carbonate, potassium carbonate, sodium bicarbonate, and potassium bicarbonate; and organic compounds such as pyridine and triethylamine. Preferable examples thereof can include sodium hydroxide, potassium hydroxide, and sodium bicarbonate.

The solvent is not particularly limited, and water, a polar organic solvent such as dimethylformamide, a nonpolar organic solvent, or the like can be used. Preferably, water or a polar organic solvent such as dimethylformamide is used. The reaction temperature is from the boiling point of the solvent used as the upper limit to equal to or higher than the melting point thereof as the lower limit and is at least 50° C. or higher, preferably between 80° C. and the boiling point inclusive, for completing the reaction in an appropriate reaction time.

The compound represented by the formula (IV) is used 0.5 to 100 times, preferably 1 to 10 times, particularly preferably 1 to 2 times the moles of the compound represented by the formula (III'). Moreover, the compound represented by the formula (III") is used 0.5 to 100 times, preferably 1 to 10 times, particularly preferably 1 to 2 times the compound represented by the formula (IX).

After the addition of the compound represented by the formula (IV) in necessary amounts to the compound represented by the formula (III'), the reaction may be performed by heating. Alternatively, the compound represented by the formula (III') is heated, and then, the compound represented by the formula (IV) may be added dropwise thereto. The former approach is preferable.

Totally the same treatment as treatment in usually performed organic synthesis is performed after the reaction. Preferably, the compound is crystallized from an organic solvent.

A mixture of compounds wherein a represents 1 to 10 may be obtained by the reaction, and the production ratios thereof differ depending on reaction conditions. Each compound can be isolated by recrystallization, column separation, etc.

Moreover, the compound represented by the formula (V) can be produced by a method shown below.

(Method A for Producing Compound Represented by the Formula (V))

A compound represented by the formula (III):

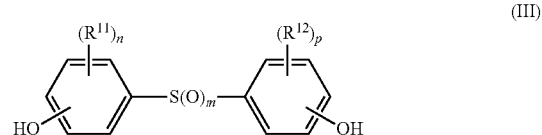

(wherein $R^{11}$, $R^{12}$, m, n, and p are as defined in the formula (I))

can be reacted with a compound represented by the formula (IV):

$$X_2CR^2COR^3 \qquad (IV)$$

(wherein $R^2$ and $R^3$ are as defined in the formula (I); and each X independently represents a halogen atom)

under alkaline conditions to produce a compound represented by the formula (V):

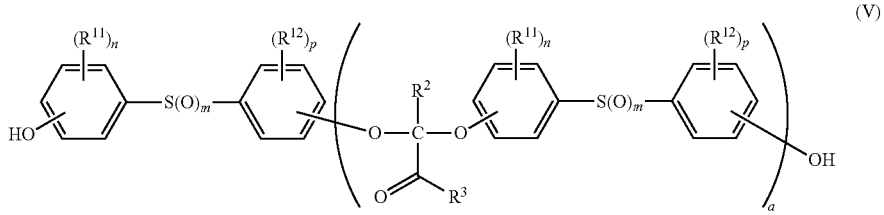

(wherein $R^2$, $R^3$, $R^{11}$, $R^{12}$, a, m, n, and p are as defined in the formula (I)).

A compound that creates the alkaline conditions is not limited, and both inorganic and organic compounds may be used. An appropriate compound is used according to a solvent used. Examples thereof can specifically include: inorganic compounds such as sodium hydroxide, potassium hydroxide, calcium hydroxide, barium hydroxide, sodium carbonate, potassium carbonate, sodium bicarbonate, and potassium bicarbonate; and organic compounds such as pyridine and triethylamine. Preferable examples thereof can include sodium hydroxide, potassium hydroxide, and sodium bicarbonate.

The reaction solvent is not particularly limited, and water, a polar organic solvent such as dimethylformamide, a nonpolar organic solvent, or the like can be used. Preferably, water or a polar organic solvent such as dimethylformamide is used. The reaction temperature is from the boiling point of the solvent used as the upper limit to equal to or higher than the melting point thereof as the lower limit. The reaction is performed at least 50° C. or higher, preferably between 80° C. and the boiling point inclusive, for completing the reaction in an appropriate reaction time.

The compound represented by the formula (IV) is used 0.0001 to 10 times, preferably 0.001 to 2 times, particularly preferably 0.1 to 1 time the moles of the compound represented by the formula (III).

After the addition of the compound represented by the formula (IV) in necessary amounts to the compound represented by the formula (III), the reaction may be performed by heating. Alternatively, the compound represented by the formula (III) is heated, and then, the compound represented by the formula (IV) may be added dropwise thereto. The former approach is preferable. Totally the same treatment as treatment in usually performed organic synthesis is performed after the reaction. Preferably, the compound is crystallized from an organic solvent.

A mixture of compounds wherein a represents 1 to 10 may be obtained by the reaction, and the production ratios thereof differ depending on reaction conditions. Each compound can be isolated by recrystallization, column separation, etc.

(Method B for Producing Compound Represented by the Formula (V))

A compound represented by the formula (VI):

(wherein $R^2$, $R^{11}$, $R^{12}$, a, m, n, and p are as defined in the formula (I))

can be reacted with a compound represented by the formula (VII):

$R^3H$            (VII)

(wherein $R^3$ is as defined in the formula (I))

under acidic conditions to produce the compound represented by the formula (V).

Examples of the compound represented by the formula (VII) can specifically include methanol, ethanol, n-propanol, isopropanol, n-butanol, sec-butanol, and t-butanol.

A compound that creates the acidic conditions is not limited, and both inorganic and organic acids may be used. An appropriate compound is used according to a solvent used. Examples thereof can specifically include: inorganic acids such as hydrochloric acid and sulfuric acid; and organic acids such as p-methyltoluenesulfonic acid. Moreover, the amount of the compound that creates the acidic conditions is not particularly limited and can be any amount that makes the reaction solution acidic. The compound may be added in necessary amounts before the reaction or may be added in additional amounts during the reaction.

A reaction solvent may not be used. The reaction solvent, when used, is not particularly limited, and the compound represented by the formula (VII) can be used as a solvent for moderately dissolving the compound represented by the formula (VI) when the compound represented by the formula (VII) is in a liquid state. Moreover, when a solvent other than the compound represented by the formula (VII) is used, specifically, toluene, xylene, n-hexane, or the like can be used. When a water-miscible solvent is used, the reaction may be performed with water as by-products discharged from the reaction system using a Dean-Stark apparatus.

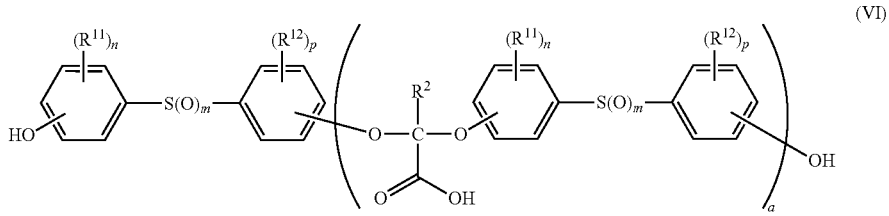

The compound represented by the formula (VI) can be produced by the method described in the method A for producing the compound represented by the formula (V). Thus, a mixture of compounds wherein a represents 1 to 10 may be obtained by the reaction. The production ratios thereof differ depending on reaction conditions. Each compound can be isolated by recrystallization, column separation, etc.

(Method C for Producing Compound Represented by the Formula (V))

A compound represented by the formula (III'):

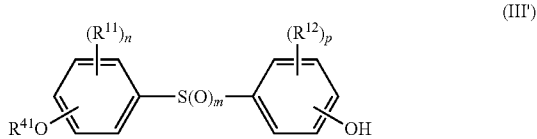

(wherein $R^{11}$, $R^{12}$, $R^{41}$, m, n, and p are as defined in the formula (I))
can be reacted with a compound represented by the formula (IV):

$$X_2CR^2COR^3 \quad (IV)$$

(wherein $R^2$ and $R^3$ are as defined in the formula (I); and each X independently represents a halogen atom)
under alkaline conditions to produce a compound represented by the formula (IX):

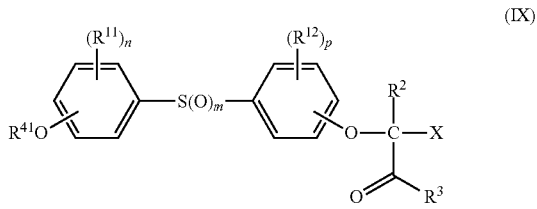

(wherein $R^2$, $R^3$, $R^{11}$, $R^{12}$, $R^{41}$, m, n, and p are as defined in the formula (I); and X is as defined in the formula (IV). Next, the compound represented by the formula (IX) can be reacted with the compound represented by the formula (III) under alkaline conditions to produce a compound represented by the formula (X):

In the reactions described above, a compound that creates the alkaline conditions is not limited, and both inorganic and organic compounds may be used. An appropriate compound is used according to a solvent used. Examples thereof can specifically include: inorganic compounds such as sodium hydroxide, potassium hydroxide, calcium hydroxide, barium hydroxide, sodium carbonate, potassium carbonate, sodium bicarbonate, and potassium bicarbonate; and organic compounds such as pyridine and triethylamine. Preferable examples thereof can include sodium hydroxide, potassium hydroxide, and sodium bicarbonate.

The solvent is not particularly limited, and water, a polar organic solvent such as dimethylformamide, a nonpolar organic solvent, or the like can be used. Preferably, water or a polar organic solvent such as dimethylformamide is used. The reaction temperature is from the boiling point of the solvent used as the upper limit to equal to or higher than the melting point thereof as the lower limit and is at least 50° C. or higher, preferably between 80° C. and the boiling point inclusive, for completing the reaction in an appropriate reaction time.

The compound represented by the formula (IV) is used 0.5 to 100 times, preferably 1 to 10 times, particularly preferably 1 to 2 times the moles of the compound represented by the formula (III'). Moreover, the compound represented by the formula (III) is used 0.5 to 100 times, preferably 1 to 10 times, particularly preferably 1 to 2 times the compound represented by the formula (IX).

After the addition of the compound represented by the formula (IV) in necessary amounts to the compound represented by the formula (III'), the reaction may be performed by heating. Alternatively, the compound represented by the formula (III') is heated, and then, the compound represented by the formula (IV) may be added dropwise thereto. The former approach is preferable.

Totally the same treatment as treatment in usually performed organic synthesis is performed after the reaction. Preferably, the compound is crystallized from an organic solvent.

A mixture of compounds wherein a represents 1 to 10 may be obtained by the reaction, and the production ratios thereof

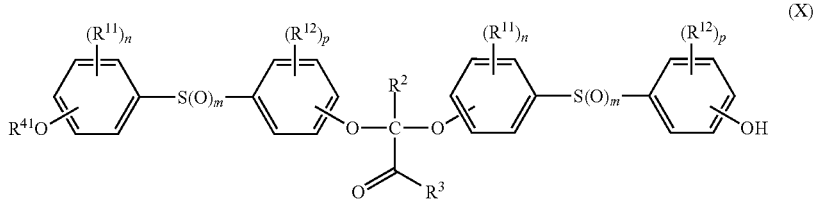

In this way, the structure having the repeat unit can be produced by sequentially reacting the compound represented by the formula (IV) with the compound represented by the formula (III).

Finally, the group $R^{41}$ can be converted to a hydroxy group by an appropriate method to produce the compound represented by the formula (V).

differ depending on reaction conditions. Each compound can be isolated by recrystallization, column separation, etc.

(Recording Material)

The recording material of the present invention can be used in any application as long as it is a recording material containing a color-forming compound and at least one compound represented by the formula (I):

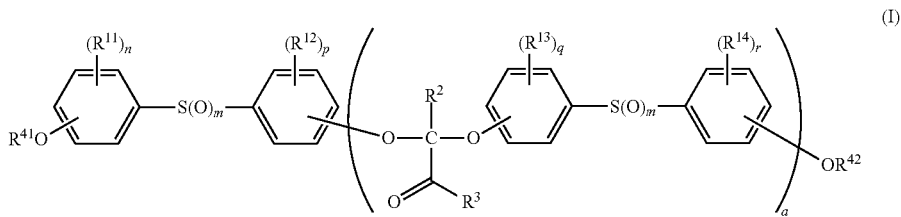

[wherein $R^{11}$ to $R^{14}$ each independently represent a halogen atom, a $C_1$-$C_6$ alkyl group, or a $C_2$-$C_6$ alkenyl group; n, q, and r each independently represent 0 or any integer of 1 to 4; m represents 0 or any integer of 1 to 2; a represents any integer of 1 to 10; $R^2$ represents a hydrogen atom or a $C_1$-$C_6$ alkyl group; $R^3$ represents a hydroxy group, an $OR^{51}$ group, a $NR^{52}R^{53}$ group, a $SR^{54}$ group, or OM; $R^{51}$ represents a $C_1$-$C_6$ alkyl group, a $C_2$-$C_6$ alkenyl group, an optionally substituted phenyl group, or an optionally substituted benzyl group; $R^{52}$ to $R^{54}$ each represent a hydrogen atom, a $C_1$-$C_6$ alkyl group, a $C_2$-$C_6$ alkenyl group, an optionally substituted phenyl group, or an optionally substituted benzyl group, and $R^{52}$ and $R^{53}$ together optionally form a saturated or unsaturated $C_4$-$C_{10}$ ring, which, optionally, further comprises heteroatom(s) (S, N, and/or O); M represents a metal atom; and $R^{41}$ and $R^{42}$ each independently represent a hydrogen atom, a $C_1$-$C_6$ alkyl group, a $C_2$-$C_6$ alkenyl group, or a protective group for the hydroxy group]. The recording material of the present invention can be used as, for example, a thermal recording material or a pressure-sensitive copying material.

The recording material is preferably a recording material containing, as the compound represented by the formula (I), at least one compound represented by the formula (II):

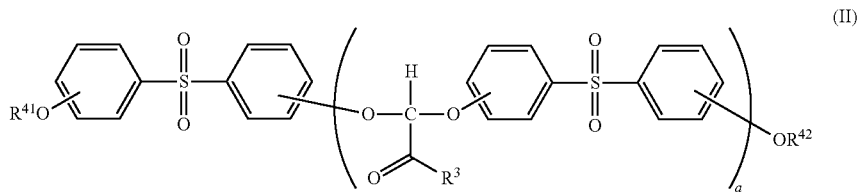

(wherein $R^3$, $R^{41}$, $R^{42}$, and a are as defined in the formula (I)), particularly preferably a recording material containing at least one phenolic compound represented by the formula (II) wherein either $R^{41}$ or $R^{42}$, or both, represent a hydrogen atom.

These phenolic compounds can be used as a color-developing agent and can be used alone or in combination of two or more thereof, as needed. The two or more phenolic compounds can be combined at any ratio.

Moreover, a composition containing two or more compounds represented by the formula (I), the compounds differing in a, can be used preferably in the recording material of the present invention.

Moreover, in the case of the composition containing two or more compounds differing in a, a reaction composition containing two or more compounds represented by the formula (V), the compounds differing in a and being obtained by reacting a compound represented by the formula (III) with a compound represented by the formula (IV), can also be used:

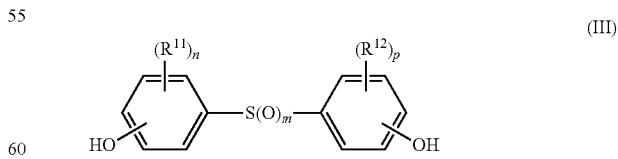

(wherein $R^{11}$, $R^{12}$, m, n, and p are as defined in the formula (I)), $$X_2CR^2COR^3 \quad (IV)$$

(wherein $R^2$ and $R^3$ are as defined in the formula (I); and each X independently represents a halogen atom), and

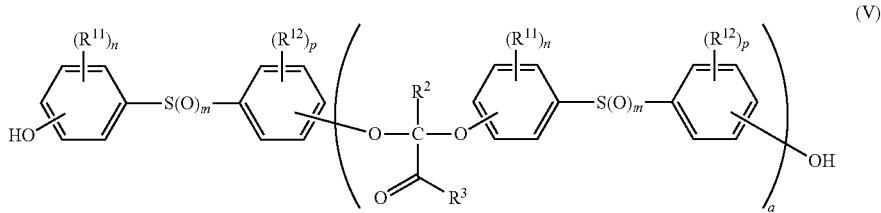

(V)

(wherein $R^2$, $R^3$, $R^{11}$, $R^{12}$, a, m, n, and p are as defined in the formula (I)).

The proportion of the compound represented by the formula (I) to the color-forming compound used is usually 0.01 to 10 parts by mass, preferably 1 to 10 parts by mass, more preferably 1.5 to 5 parts by mass, with respect to 1 part by mass of the color-forming compound.

(Other Components in Recording Material)

The recording material of the present invention can contain, in addition to the color-forming compound and the compound represented by the formula (I), one or two or more color-developing agents, image stabilizers, sensitizers, fillers, dispersants, antioxidants, desensitizers, anti-tack agents, antifoaming agents, light stabilizers, fluorescent brightening agents, etc., known in the art, as needed. The amount of each component used is in the range of usually 0.1 to 15 parts by mass, preferably 1 to 10 parts by mass, with respect to 1 part by mass of the color-forming compound.

These agents may be contained in a color-developing layer or may be contained in any layer, for example, a protective layer, when they consist of a multilayer structure. Particularly, when an overcoat layer or an undercoat layer is provided in the upper and/or lower parts of the color-developing layer, these layers can contain antioxidants, light stabilizers, etc. Furthermore, these antioxidants or light stabilizers can be contained in a form encapsulated in microcapsules, as needed, in these layers.

Examples of the color-forming compound used in the recording material of the present invention can include, but not limited to, fluoran, phthalide, lactam, triphenylmethane, phenothiazine, and spiropyran leuco dyes. Any color-forming compound that forms a color by contact with the color-developing agent, which is an acidic substance, can be used. Moreover, these color-forming compounds can be used alone to produce a recording material with the color to be formed, as a matter of course. Alternatively, two or more thereof can be mixed for use. For example, three primary color (red, blue, and green)-forming compounds or black color-forming compounds can be mixed and used to produce a recording material that develops a true black color.

Examples of the color-forming fluoran compounds include 3,3-bis(p-dimethylaminophenyl)-phthalide, 3,3-bis(p-dimethylaminophenyl)-6-dimethylaminophthalide (also known as crystal violet lactone), 3,3-bis(p-dimethylaminophenyl)-6-diethylaminophthalide, 3,3-bis(p-dimethylaminophenyl)-6-chlorophthalide, 3,3-bis(p-dibutylaminophenyl)-phthalide, 3-cyclohexylamino-6-chlorofluoran, 3-dimethylamino-5,7-dimethylfluoran, 3-N-methyl-N-isopropylamino-6-methyl-7-anilinofluoran, 3-N-methyl-N-isobutylamino-6-methyl-7-anilinofluoran, 3-N-methyl-N-isoamylamino-6-methyl-7-anilinofluoran, 3-diethylamino-7-chlorofluoran, 3-diethylamino-6,8-dimethylfluoran, 3-diethylamino-7-methylfluoran, 3-diethylamino-7,8-benzofluoran, 3-diethylamino-6-methyl-7-chlorofluoran, 3-dibutylamino-6-methyl-7-bromofluoran, 3-(N-p-tolyl-N-ethylamino)-6-methyl-7-anilinofluoran, 3-pyrrolidino-6-methylamino-7-anilinofluoran, 2-{N-(3'-trifluoromethylphenyl)amino}-6-diethylaminofluoran, 2-{3,6-bis(diethylamino)-9-(o-chloroanilino)xanthylbenzoic acid lactam}, 3-diethylamino-6-methyl-7-(m-trichloromethylanilino)fluoran, 3-diethylamino-7-(o-chloroanilino)fluoran, 3-dibutylamino-7-(o-chloroanilino)fluoran, 3-N-methyl-N-amylamino-6-methyl-7-anilinofluoran, 3-N-methyl-N-cyclohexylamino-6-methyl-7-anilinofluoran, 3-diethylamino-6-methyl-7-anilinofluoran, 3-diethylamino-6-methyl-7-(2',4'-dimethylanilino)fluoran, 3-(N,N-diethylamino)-5-methyl-7-(N,N-dibenzylamino)fluoran, 3-(N,N-diethylamino)-7-(N,N-dibenzylamino)fluoran, 3-(N-ethyl-N-isobutylamino)-6-methyl-7-anilinofluoran, 3-(N-ethyl-N-propylamino)-6-methyl-7-anilinofluoran, 3-(N-methyl-N-propylamino)-6-methyl-7-anilinofluoran, 3-(N-ethyl-N-isopentylamino)-6-methyl-7-anilinofluoran, 3-(N-ethyl-N-toluidino)-6-methyl-7-anilino-fluoran, 3-pyrrolidino-6-methyl-7-anilinofluoran, 3-piperidino-6-methyl-7-anilinofluoran, 3-dimethylamino-7-(m-trifluoromethylanilino)fluoran, 3-dipentylamino-6-methyl-7-anilinofluoran, 3-(N-ethoxypropyl-N-ethylamino)-6-methyl-7-anilinofluoran, 3-dibutylamino-7-(o-fluoroanilino)fluoran, 3-diethylaminobenzo[a]fluoran, 3-diethylamino-5-methyl-7-benzylaminofluoran, 3-diethylamino-5-chlorofluoran, 3-diethylamino-6-(N,N'-dibenzylamino)fluoran, 3,6-dimethoxyfluoran, 2,4-dimethyl-6-(4-dimethylaminophenyl)aminofluoran, 3-diethylamino-7-(m-trifluoromethylanilino)fluoran, 3-diethylamino-6-methyl-7-octylaminofluoran, 3-diethylamino-6-methyl-7-(m-tolylamino)fluoran, 3-diethylamino-6-methyl-7-(2,4-xylylamino)fluoran, 3-diethylamino-7-(o-fluoroanilino)fluoran, 3-diphenylamino-6-methyl-7-anilinofluoran, benzoylleucomethylene blue, 6'-chloro-8'-methoxy-benzindolino-spiropyran, 6'-bromo-3'-methoxy-benzindolino-spiropyran, 3-(2'-hydroxy-4'-dimethylaminophenyl)-3-(2'-methoxy-5'-chlorophenyl)phthalide, 3-(2'-hydroxy-4'-dimethylaminophenyl)-3-(2'-methoxy-5'-nitrophenyl)phthalide, 3-(2'-hydroxy-4'-diethylaminophenyl)-3-(2'-methoxy-5'-methylphenyl)phthalide, 3-(2'-methoxy-4'-dimethylaminophenyl)-3-(2'-hydroxy-4'-chloro-5'-methylphenyl)phthalide, 3-morpholino-7-(N-propyl-trifluoromethylanilino) fluoran, 3-pyrrolidino-7-trifluoromethylanilinofluoran, 3-diethylamino-5-chloro-7-(N-benzyl-trifluoromethylanilino)fluoran, 3-pyrrolidino-7-(di-p-chlorophenyl)methylaminofluoran, 3-diethylamino-5-chloro-7-(α-phenylethylamino)fluoran, 3-(N-ethyl-p-toluidino)-7-(α-phenylethylamino)fluoran, 3-diethylamino-7-(o-methoxycarbonylphenylamino)fluoran, 3-diethylamino-5-methyl-7-(α-phenylethylamino)fluoran, 3-diethylamino-7-piperidinofluoran, 2-chloro-3-(N-methyl-toluidino)-7-(p-n-butylanilino)fluoran, 3-(N-methyl-N-isopropylamino)-6-methyl-7-anilinofluoran, 3-dibutylamino-6-methyl-7-anilinofluoran, 3-dipentylamino-6-methyl-7-anilinofluoran, 3,6-bis(dimethylamino)fluorenespiro(9,3')-6'-dimethylaminophthalide, 3-(N-benzyl-N- cyclohexylamino)-5,6-benzo-7-α-naphthylamino-4'-bromofluoran, 3-diethylamino-6-chloro-7-anilinofluoran, 3-N-ethyl-N-(2-ethoxypropyl)amino-6-methyl-7-anilinofluoran, 3-N-ethyl-N-tetrahydrofurfurylamino-6-methyl-7-anilinofluoran, 3-diethylamino-6-methyl-7-mesidino-4',5'-benzofluoran, and 3-(N-ethyl-p-toluidino)-7-(methylphenylamino)fluoran.

Among these color-forming compounds, preferable examples thereof can include 3,3-bis(p-dimethylaminophenyl)-6-dimethylaminophthalide, 3-cyclohexylamino-6-chlorofluoran, 3-diethylamino-7-chlorofluoran, 3-diethylamino-6,8-dimethylfluoran, 3-diethylamino-7-methylfluoran, 3-diethylamino-7,8-benzofluoran, 3-diethylamino-6-methyl-7-chlorofluoran, 3-dibutylamino-6-methyl-7-bromofluoran, 3-diethylamino-7-(o-chloroanilino)fluoran, 3-dibutylamino-7-(o-chloroanilino)fluoran, 3-N-methyl-N-cyclohexylamino-6-methyl-7-anilinofluoran, 3-(N,N-diethylamino)-5-methyl-7-(N,N-dibenzylamino)fluoran, 3-(N,N-diethylamino)-7-(N,N-dibenzylamino)fluoran, 3-(N-ethyl-N-isobutylamino)-6-methyl-7-anilinofluoran, 3-(N-methyl-N-propylamino)-6-methyl-7-anilinofluoran, 3-(N-ethyl-N-isopentylamino)-6-methyl-7-anilinofluoran, 3-(N-ethyl-N-toluidino)-6-methyl-7-anilino-fluoran, 3-(N-ethoxypropyl-N-ethylamino)-6-methyl-7-anilinofluoran, 3-dibutylamino-7-(o-fluoroanilino)fluoran, 3-diethylamino-7-(m-trifluoromethylanilino)fluoran, 3-diethylamino-6-methyl-7-octylaminofluoran, 3-diethylamino-6-methyl-7-(m-tolylamino)fluoran, 3-diethylamino-7-(o-fluoroanilino)fluoran, 3-diphenylamino-6-methyl-7-anilinofluoran, benzoylleucomethylene blue, 3-dibutylamino-6-methyl-7-anilinofluoran, 3-N-ethyl-N-tetrahydrofurfurylamino-6-methyl-7-anilinofluoran, and 3-(N-ethyl-p-toluidino)-7-(methylphenylamino)fluoran.

Moreover, examples of near infrared absorbing dyes include 3-[4-[4-(4-anilino)-anilino]anilino]-6-methyl-7-chlorofluoran, 3,3-bis[2-(4-dimethylaminophenyl)-2-(4-methoxyphenyl)vinyl]-4,5,6,7-tetrachlorophthalide, and 3,6,6'-tris(dimethylamino)spiro(fluorene-9,3'-phthalide).

The compound of the present invention represented by the formula (I) is preferably used as a color-developing agent, mainly in a thermal recording material and may be used alone or in combination with a plurality of color-developing agents known in the art. They can be combined at any ratio.

Examples of other color-developing agents can specifically include the followings:
bisphenol compounds such as bisphenol A, 4,4'-sec-butylidenebisphenol, 4,4'-cyclohexylidenebisphenol, 2,2'-bis(4-hydroxyphenyl)-3,3'-dimethylbutane, 2,2'-dihydroxydiphenyl, pentamethylene-bis(4-hydroxybenzoate), 2,2-dimethyl-3,3-di(4-hydroxyphenyl)pentane, 2,2-di(4-hydroxyphenyl)hexane, 2,2-bis(4-hydroxyphenyl)propane, 2,2-bis(4-hydroxyphenyl)butane, 2,2-bis(4-hydroxy-3-methylphenyl)propane, 4,4'-(1-phenylethylidene)bisphenol, 4,4'-ethylidenebisphenol, (hydroxyphenyl)methylphenol, 2,2'-bis(4-hydroxy-3-phenyl-phenyl)propane, 4,4'-(1,3-phenylenediisopropylidene)bisphenol, 4,4'-(1,4-phenylenediisopropylidene)bisphenol, and butyl 2,2-bis(4-hydroxyphenyl)acetate;
sulfur-containing bisphenol compounds such as 4,4'-dihydroxydiphenyl thioether, 1,7-di(4-hydroxyphenylthio)-3,5-dioxaheptane, 2,2'-bis(4-hydroxyphenylthio)diethyl ether, and 4,4'-dihydroxy-3,3'-dimethyldiphenyl thioether; 4-hydroxybenzoic acid esters such as benzyl 4-hydroxybenzoate, ethyl 4-hydroxybenzoate, propyl 4-hydroxybenzoate, isopropyl 4-hydroxybenzoate, butyl 4-hydroxybenzoate, isobutyl 4-hydroxybenzoate, chlorobenzyl 4-hydroxybenzoate, methylbenzyl 4-hydroxybenzoate, and diphenylmethyl 4-hydroxybenzoate;
metal salts of benzoic acid such as zinc benzoate and zinc 4-nitrobenzoate; salicylic acids such as 4-[2-(4-methoxyphenyloxy)ethyloxy]salicylic acid;
metal salts of salicylic acid such as zinc salicylate and zinc bis[4-(octyloxycarbonylamino)-2-hydroxybenzoate];
hydroxysulfones such as 4,4'-dihydroxydiphenylsulfone, 2,4'-dihydroxydiphenylsulfone, 4-hydroxy-4'-methyldiphenylsulfone, 4-hydroxy-4'-isopropoxydiphenylsulfone, 4-hydroxy-4'-butoxydiphenylsulfone, 4,4'-dihydroxy-3,3'-diallyldiphenylsulfone, 3,4-dihydroxy-4'-methyldiphenylsulfone, 4,4'-dihydroxy-3,3',5,5'-tetrabromodiphenylsulfone, 4-allyloxy-4'-hydroxydiphenylsulfone, 2-(4-hydroxyphenylsulfonyl)phenol, 4,4'-sulfonylbis[2-(2-propenyl)]phenol, 4-[[4-(propoxy)phenyl]sulfonyl]phenol, 4-[{4-(allyloxy)phenyl}sulfonyl]phenol, 4-[{4-(benzyloxy)phenyl}sulfonyl]phenol, and 2,4-bis(phenylsulfonyl)-5-methyl-phenol;
polyvalent metal salts of hydroxysulfones such as 4-phenylsulfonylphenoxy-zinc magnesium, -aluminum, and -titanium;
4-hydroxyphthalic acid diesters such as dimethyl 4-hydroxyphthalate, dicyclohexyl 4-hydroxyphthalate, and diphenyl 4-hydroxyphthalate;
hydroxynaphthoic acid esters such as 2-hydroxy-6-carboxynaphthalene;
trihalomethylsulfones such as tribromomethylphenylsulfone;
sulfonylureas such as 4,4'-bis(p-toluenesulfonylaminocarbonylamino)diphenylmethane and N-(4-methylphenylsulfonyl)-N'-(3-(4-methylphenylsulfonyloxy)phenyl)urea;
hydroxyacetophenone, p-phenylphenol, benzyl 4-hydroxyphenylacetate, p-benzylphenol, hydroquinone-monobenzyl ether, 2,4-dihydroxy-2'-methoxybenzanilide, tetracyanoquinodimethanes, N-(2-hydroxyphenyl)-2-[(4-hydroxyphenyl)thio]acetamide, N-(4-hydroxyphenyl)-2-[(4-hydroxyphenyl)thio]acetamide, 4-hydroxybenzenesulfonanilide, 4'-hydroxy-4-methylbenzenesulfonanilide, 4,4'-bis(4-methyl-3-phenoxycarbonyl)aminophenylureido)))diphenylsulfone, 3-(3-phenylureido)benzenesulfonanilide, octadecylphosphoric acid, and dodecylphosphoric acid; and
cross-linked diphenylsulfone compounds represented by the following formula or mixtures thereof:

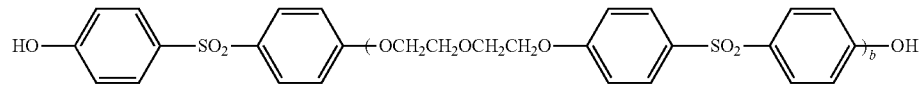

b represents an integer of 0 to 6.

Among them, preferable examples thereof include 4-hydroxy-4'-isopropoxydiphenylsulfone and cross-linked diphenylsulfone compounds or mixtures thereof.

Examples of the image stabilizer can include:
epoxy group-containing diphenylsulfones such as 4-benzyloxy-4'-(2-methylglycidyloxy)-diphenylsulfone and 4,4'-diglycidyloxydiphenylsulfone;
1,4-diglycidyloxybenzene, 4-[α-(hydroxymethyl)benzyloxy]-4'-hydroxydiphenylsulfone, 2-propanol derivatives, salicylic acid derivatives, metal salts (particularly, zinc salts)

of oxynaphthoic acid derivatives, metal salts of 2,2-methylenebis(4,6-t-butylphenyl)phosphate, and other water-insoluble zinc compounds;

hindered phenol compounds such as 2,2-bis(4'-hydroxy-3',5'-dibromophenyl)propane, 4,4'-sulfonylbis(2,6-dibromophenol), 4,4'-butylidene(6-t-butyl-3-methylphenol), 2,2'-methylene-bis(4-methyl-6-t-butylphenol), 2,2'-methylene-bis(4-ethyl-6-t-butylphenol), 2,2'-di-t-butyl-5,5'-dimethyl-4,4'-sulfonyldiphenol, 1,1,3-tris(2-methyl-4-hydroxy-5-cyclohexylphenyl)butane, and 1,1,3-tris(2-methyl-4-hydroxy-5-t-butylphenyl)butane; and phenol novolac compounds, and epoxy resins.

The image stabilizer is preferably a compound that is solid at room temperature, particularly preferably has a melting point of 60° C. or higher, and is poorly soluble in water.

Examples of the sensitizer can include:

higher fatty acid amides such as stearic acid amide, stearic acid anilide, and palmitic acid amide;

amides such as benzamide, acetoacetic acid anilide, thioacetanilide acrylic acid amide, ethylenebisamide, ortho-toluenesulfonamide, and para-toluenesulfonamide;

phthalic acid diesters such as dimethyl phthalate, dibenzyl isophthalate, dimethyl isophthalate, dimethyl terephthalate, diethyl isophthalate, diphenyl isophthalate, and dibenzyl terephthalate;

oxalic acid diesters such as dibenzyl oxalate, di(4-methylbenzyl)oxalate, di(4-chlorobenzyl)oxalate, a mixture of benzyl oxalate and di(4-chlorobenzyl)oxalate in equal amounts, and a mixture of di(4-chlorobenzyl)oxalate and di(4-methylbenzyl) oxalate in equal amounts;

bis(t-butylphenols) such as 2,2'-methylenebis(4-methyl-6-t-butylphenol) and 4,4'-methylene-bis-2,6-di-t-butylphenol;

4,4'-dihydroxydiphenylsulfone diethers such as 4,4'-dimethoxydiphenylsulfone, 4,4'-diethoxydiphenylsulfone, 4,4'-dipropoxydiphenylsulfone, 4,4'-diisopropoxydiphenylsulfone, 4,4'-dibutoxydiphenylsulfone, 4,4'-diisobutoxydiphenylsulfone, 4,4'-dipentyloxydiphenylsulfone, 4,4'-dihexyloxydiphenylsulfone, and 4,4'-diallyloxydiphenylsulfone;

2,4'-dihydroxydiphenylsulfone diethers such as 2,4'-dimethoxydiphenylsulfone, 2,4'-diethoxydiphenylsulfone, 2,4'-dipropoxydiphenylsulfone, 2,4'-diisopropoxydiphenylsulfone, 2,4'-dibutoxydiphenylsulfone, 2,4'-diisobutoxydiphenylsulfone, 2,4'-dipentyloxydiphenylsulfone, 2,4'-dihexyloxydiphenylsulfone, and 2,4'-diallyloxydiphenylsulfone;

terphenyls such as m-terphenyl and p-terphenyl;

carbonic acid derivatives such as diphenyl carbonate, guaiacol carbonate, di-p-tolyl carbonate, and phenyl-α-naphthyl carbonate;

1,2-bis(phenoxy)ethane, 1,2-bis(4-methylphenoxy)ethane, 1,2-bis(3-methylphenoxy)ethane, 1,2-bis(phenoxymethyl)benzene, 1,2-bis(4-methoxyphenylthio)ethane, 1,2-bis(4-methoxyphenoxy)propane, 1,3-phenoxy-2-propanol, 1,4-diphenylthio-2-butene, 1,4-diphenylthiobutane, 1,4-diphenoxy-2-butene, 1,5-bis(4-methoxyphenoxy)-3-oxapentane, 1,3-dibenzoyloxypropane, dibenzoyloxymethane, 4,4'-ethylenedioxy-bis-benzoic acid dibenzyl ester, bis[2-(4-methoxy-phenoxy)ethyl]ether, 2-naphthylbenzyl ether, 1,3-bis(2-vinyloxyethoxy)benzene, 1,4-diethoxynaphthalene, 1,4-dibenzyloxynaphthalene, 1,4-dimethoxynaphthalene, 1,4-bis(2-vinyloxyethoxy)benzene, p-(2-vinyloxyethoxy) biphenyl, p-aryloxybiphenyl, p-propargyloxybiphenyl, p-benzyloxybenzyl alcohol, 4-(m-methylphenoxymethyl)biphenyl, 4-methylphenyl-biphenyl ether, di-β-naphthylphenylenediamine, diphenylamine, carbazole, 2,3-di-m-tolylbutane, 4-benzylbiphenyl, 4,4'-dimethylbiphenyl, 1,2-bis(3,4-dimethylphenyl)ethane, 2,3,5,6-tetramethyl-4'-methyldiphenylmethane, 4-acetylbiphenyl, dibenzoylmethane, triphenylmethane, phenyl 1-hydroxy-naphthoate, methyl 1-hydroxy-2-naphthoate, N-octadecylcarbamoyl-p-methoxycarbonylbenzene, benzyl p-benzyloxybenzoate, phenyl β-naphthoate, methyl p-nitrobenzoate, diphenylsulfone, 1,1-diphenylpropanol, 1,1-diphenylethanol, N-octadecylcarbamoylbenzene, dibenzyl disulfide, stearic acid, Amide AP-1 (7:3 mixture of stearic acid amide and palmitic acid amide), stearates such as aluminum stearate, calcium stearate, and zinc stearate; and zinc palmitate, behenic acid, zinc behenate, montanic acid wax, and polyethylene wax.

Preferable examples thereof can include 2-naphthylbenzyl ether, m-terphenyl, 4-benzylbiphenyl, benzyl oxalate, di(4-chlorobenzyl)oxalate, a mixture of benzyl oxalate and di(4-chlorobenzyl)oxalate in equal amounts, di(4-methylbenzyl)oxalate, a mixture of di(4-chlorobenzyl)oxalate and di(4-methylbenzyl)oxalate in equal amounts, phenyl 1-hydroxy-2-naphthoate, 1,2-bis(phenoxy)ethane, 1,2-bis-(3-methylphenoxy)ethane, 1,2-bis(phenoxymethyl)benzene, dimethyl terephthalate, stearic acid amide, Amide AP-1 (7:3 mixture of stearic acid amide and palmitic acid amide), diphenylsulfone, and 4-acetylbiphenyl.

More preferable examples thereof can include di(4-methylbenzyl)oxalate, 1,2-bis(3-methylphenoxy)ethane, 1,2-bis(phenoxymethyl)benzene, diphenylsulfone, and 2-naphthylbenzyl ether.

Examples of the filler can include silica, clay, kaolin, fired kaolin, talc, satin white, aluminum hydroxide, calcium carbonate, magnesium carbonate, zinc oxide, titanium oxide, barium sulfate, magnesium silicate, aluminum silicate, plastic pigments, diatomaceous earth, talc, and aluminum hydroxide. Among them, preferable examples thereof can include alkaline earth metal salts, particularly, carbonates such as calcium carbonate and magnesium carbonate. The proportion of the filler used is 0.1 to 15 parts by mass, preferably 1 to 10 parts by mass, with respect to 1 part by mass of the color-forming compound. Moreover, these fillers may be mixed for use.

Examples of the dispersant can include: polyvinyl alcohols having various degrees of saponification and polymerization, such as polyvinyl alcohol, acetoacetylated polyvinyl alcohol, carboxy-modified polyvinyl alcohol, sulfonic acid-modified polyvinyl alcohol, amide-modified polyvinyl alcohol, and butyral-modified vinyl alcohol; cellulose derivatives such as methylcellulose, carboxymethylcellulose, hydroxyethylcellulose, ethylcellulose, acetylcellulose, and hydroxymethylcellulose; and sodium polyacrylate, polyacrylic acid ester, polyacrylamide, starch, sulfosuccinic acid esters such as dioctyl sodium sulfosuccinate, sodium dodecylbenzenesulfonate, a sodium salt of lauryl alcohol sulfonic acid ester, fatty acid salt, styrene-maleic anhydride copolymers, styrene-butadiene copolymers, polyvinyl chloride, polyvinyl acetate, polyacrylic acid ester, polyvinylbutyral, polyurethane, polystyrene and copolymers thereof, polyamide resins, silicone resins, petroleum resins, terpene resins, ketone resins, and coumarone resins.

The dispersant is used after being dissolved in a solvent such as water, alcohol, ketone, ester, or hydrocarbon. Alternatively, the dispersant may be used in a state emulsified in water or other solvents or in the form of paste dispersed therein.

Examples of the antioxidant can include 2,2'-methylenebis(4-methyl-6-t-butylphenol), 2,2'-methylenebis(4-ethyl-6-t-butylphenol), 4,4'-propylmethylenebis(3-methyl-6-t-butylphenol), 4,4'-butylidenebis(3-methyl-6-t-butylphenol), 4,4'-thiobis(2-t-butyl-5-methylphenol), 1,1,3-tris(2-methyl-4-hydroxy-5-t-butylphenyl)butane, 1,1,3-tris(2-methyl-4-hydroxy-5-cyclohexylphenyl)butane, 4-{4-[1,1-bis(4-hydroxyphenyl)ethyl]-α,α-dimethylbenzyl}phenol, 1,1,3-tris(2-methyl-4-hydroxy-5-cyclohexylphenyl)butane, 2,2'-methylenebis(6-tert-butyl-4-methylphenol), 2,2'-methylenebis(6-tert-butyl-4-ethylphenol), 4,4'-thiobis(6-tert-butyl-3-methylphenol), 1,3,5-tris[{4-(1,1-dimethylethyl)-3-hydroxy-2,6-dimethylphenyl}methyl]-1,3,5-triazine-2,4,6(1H,3H,5H)-trione, and 1,3,5-tris[{3,5-bis(1,1-dimethylethyl)-4-hydroxyphenyl}methyl]-1,3,5-triazine-2,4,6(1H,3H,5H)-trione.

Examples of the desensitizer can include aliphatic higher alcohols, polyethylene glycol, and guanidine derivatives.

Examples of the anti-tack agent can include stearic acid, zinc stearate, calcium stearate, carnauba wax, paraffin wax, and ester wax.

Examples of the antifoaming agent can include higher alcohol, fatty acid ester, oil, silicone, polyether, modified hydrocarbon, and paraffin antifoaming agents.

Examples of the light stabilizer can include: salicylic acid UV absorbers such as phenyl salicylate, p-t-butylphenyl salicylate, and p-octylphenyl salicylate; benzophenone UV absorbers such as 2,4-dihydroxybenzophenone, 2-hydroxy-4-methoxybenzophenone, 2-hydroxy-4-benzyloxybenzophenone, 2-hydroxy-4-octyloxybenzophenone, 2-hydroxy-4-dodecyloxybenzophenone, 2,2'-dihydroxy-4-methoxybenzophenone, 2,2'-dihydroxy-4,4'-dimethoxybenzophenone, 2-hydroxy-4-methoxy-5-sulfobenzophenone, and bis(2-methoxy-4-hydroxy-5-benzoylphenyl)methane;
benzotriazole UV absorbers such as 2-(2'-hydroxy-5'-methylphenyl)benzotriazole, 2-(2'-hydroxy-5'-t-butylphenyl)benzotriazole, 2-(2'-hydroxy-3',5'-di-t-butylphenyl)benzotriazole, 2-(2'-hydroxy-3'-t-butyl-5'-methylphenyl)-5-chlorobenzotriazole, 2-(2'-hydroxy-3',5'-di-t-butylphenyl)-5-chlorobenzotriazole, 2-(2'-hydroxy-3',5'-di-t-amylphenyl)benzotriazole, 2-(2'-hydroxy-5'-tert-butylphenyl)benzotriazole, 2-(2'-hydroxy-5'-(1'',1'',3'',3''-tetramethylbutyl)phenyl)benzotriazole, 2-[2'-hydroxy-3'-(3'',4'',5'',6''-tetrahydrophthalimidomethyl)-5'-methylphenyl]benzotriazole, 2-(2'-hydroxy-5'-t-octylphenyl)benzotriazole, 2-[2'-hydroxy-3',5'-bis(α,α-dimethylbenzyl)phenyl]-2H-benzotriazole, 2-(2'-hydroxy-3'-dodecyl-5'-methylphenyl)benzotriazole, 2-(2'-hydroxy-3'-undecyl-5'-methylphenyl)benzotriazole, 2-(2'-hydroxy-3'-tridecyl-5'-methylphenyl)benzotriazole, 2-(2'-hydroxy-3'-tetradecyl-5'-methylphenyl)benzotriazole, 2-(2'-hydroxy-3'-pentadecyl-5'-methylphenyl)benzotriazole, 2-(2'-hydroxy-3'-hexadecyl-5'-methylphenyl)benzotriazole, 2-[2'-hydroxy-4'-(2''-ethylhexyl)oxyphenyl]benzotriazole, 2-[2'-hydroxy-4'-(2''-ethylheptyl)oxyphenyl]benzotriazole, 2-[2'-hydroxy-4'-(2''-ethyloctyl)oxyphenyl]benzotriazole, 2-[2'-hydroxy-4'-(2''-propyloctyl)oxyphenyl]benzotriazole, 2-[2'-hydroxy-4'-(2''-propylheptyl)oxyphenyl]benzotriazole, 2-[2'-hydroxy-4'-(2''-propylhexyl)oxyphenyl]benzotriazole, 2-[2'-hydroxy-4'-(1''-ethylhexyl)oxyphenyl]benzotriazole, 2-[2'-hydroxy-4'-(1''-ethylheptyl)oxyphenyl]benzotriazole, 2-[2'-hydroxy-4'-(1''-ethyloctyl)oxyphenyl]benzotriazole, 2-[2'-hydroxy-4'-(1''-propyloctyl)oxyphenyl]benzotriazole, 2-[2'-hydroxy-4'-(1''-propylheptyl)oxyphenyl]benzotriazole, 2-[2'-hydroxy-4'-(1''-propylhexyl)oxyphenyl]benzotriazole, 2,2'-methylenebis[4-(1,1,3,3-tetramethylbutyl)-6-(2H-benzotriazol-2-yl)]phenol, and a condensate of polyethylene glycol and methyl-3-[3-t-butyl-5-(2H-benzotriazol-2-yl)-4-hydroxyphenyl]propionate;
cyanoacrylate UV absorbers such as 2'-ethylhexyl-2-cyano-3,3-diphenylacrylate and ethyl-2-cyano-3,3-diphenylacrylate;
hindered amine UV absorbers such as bis(2,2,6,6-tetramethyl-4-piperidyl)sebacate, succinic acid-bis(2,2,6,6-tetramethyl-4-piperidyl) ester, and 2-(3,5-di-t-butyl)malonic acid-bis(1,2,2,6,6-pentamethyl-4-piperidyl) ester; and 1,8-dihydroxy-2-acetyl-3-methyl-6-methoxynaphthalene.

Examples of the fluorescent brightening agent can include 4,4'-bis[2-anilino-4-(2-hydroxyethyl)amino-1,3,5-triazinyl-6-amino]stilbene-2,2'-disulfonic acid disodium salt, 4,4'-bis[2-anilino-4-bis(hydroxyethyl)amino-1,3,5-triazinyl-6-amino]stilbene-2,2'-disulfonic acid disodium salt, 4,4'-bis[2-anilino-4-bis(hydroxypropyl)amino-1,3,5-triazinyl-6-amino]stilbene-2,2'-disulfonic acid disodium salt, 4,4'-bis[2-methoxy-4-(2-hydroxyethyl)amino-1,3,5-triazinyl-6-amino]stilbene-2,2'-disulfonic acid disodium salt, 4,4'-bis[2-methoxy-4-(2-hydroxypropyl)amino-1,3,5-triazinyl-6-amino]stilbene-2,2'-disulfonic acid disodium salt, 4,4'-bis[2-m-sulfoanilino-4-bis(hydroxyethyl)amino-1,3,5-triazinyl-6-amino]stilbene-2,2'-disulfonic acid disodium salt, 4-[2-p-sulfoanilino-4-bis(hydroxyethyl)amino-1,3,5-triazinyl-6-amino]-4'-[2-m-sulfoanilino-4-bis(hydroxyethyl)amino-1,3,5-triazinyl-6-amino]stilbene-2,2'-disulfonic acid tetrasodium salt, 4,4'-bis[2-p-sulfoanilino-4-bis(hydroxyethyl)amino-1,3,5-triazinyl-6-amino]stilbene-2,2'-disulfonic acid tetrasodium salt, 4,4'-bis[2-(2,5-disulfoanilino)-4-phenoxyamino-1,3,5-triazinyl-6-amino]stilbene-2,2'-disulfonic acid hexasodium salt, 4,4'-bis[2-(2,5-disulfoanilino)-4-(p-methoxycarbonylphenoxy)amino-1,3,5-triazinyl-6-amino]stilbene-2,2'-disulfonic acid hexasodium salt, 4,4'-bis[2-(p-sulfophenoxy)-4-bis(hydroxyethyl)amino-1,3,5-triazinyl-6-amino]stilbene-2,2'-disulfonic acid hexasodium salt, 4,4'-bis[2-(2,5-disulfoanilino)-4-formalinylamino-1,3,5-triazinyl-6-amino]stilbene-2,2'-disulfonic acid hexasodium salt, and 4,4'-bis[2-(2,5-disulfoanilino)-4-bis(hydroxyethyl)amino-1,3,5-triazinyl-6-amino]stilbene-2,2'-disulfonic acid hexasodium salt.

(Method for Producing Recording Material)

When the compound of the present invention is used in thermal recording paper, it may be used in the same way as a known use method. For example, the thermal recording paper can be produced by separately dispersing fine particles of the compound of the present invention and fine particles of a color-forming compound in aqueous solutions of water-soluble binders such as polyvinyl alcohol or cellulose, mixing these suspension solutions, applying the mixture to a support such as paper, and drying it.

The proportion of the compound represented by the formula (I) to the color-forming compound used is usually 0.01 to 10 parts by mass, preferably 1 to 10 parts by mass, more preferably 1.5 to 5 parts by mass, with respect to 1 part by mass of the color-forming compound.

When the compound of the present invention is used in pressure-sensitive copying paper, it can be produced in the same way as in use of a known color-developing agent or sensitizer. For example, a color-forming compound microencapsulated by a method known in the art is dispersed in an appropriate dispersant and applied to paper to prepare a sheet of the color-forming compound. Moreover, a dispersion solution of a color-developing agent is applied to paper to prepare a sheet of the color-developing agent. In this case, the compound of the present invention, when used as an image stabilizer, may be dispersed, for use, in either of the dispersion solutions for the sheets of the color-forming compound and the color-developing agent. Both the sheets thus prepared are combined to prepare pressure-sensitive copying paper. The pressure-sensitive copying paper may be a unit consisting of: upper paper carrying a microcapsule containing a solution of a color-forming compound in an organic solvent, wherein the microcapsule is applied on the underside of the upper paper; and lower paper carrying a color-developing agent (acidic substance) applied on the top surface of the lower paper. Alternatively, the pressure-sensitive copying paper may be so-called self-contained paper comprising the microcapsule and the color-developing agent applied on the same paper surface.

Those conventionally known are used as the color-developing agent used in the production or the color-developing agent mixed with the compound of the present invention for use. Examples thereof can include: inorganic acidic substances such as Japanese acid clay, activated clay, attapulgite, bentonite, colloidal silica, aluminum silicate, magnesium silicate, zinc silicate, tin silicate, fired kaolin, and talc; aliphatic carboxylic acids such as oxalic acid, maleic acid, tartaric acid, citric acid, succinic acid, and stearic acid; aromatic carboxylic acids such as benzoic acid, p-t-butylbenzoic acid, phthalic acid, gallic acid, salicylic acid, 3-isopropylsalicylic acid, 3-phenylsalicylic acid, 3-cyclohexylsalicylic acid, 3,5-di-t-butylsalicylic acid, 3-methyl-5-benzylsalicylic acid, 3-phenyl-5-(2,2-dimethylbenzyl)salicylic acid, 3,5-di-(2-methylbenzyl)salicylic acid, and 2-hydroxy-1-benzyl-3-naphthoic acid, and metal (e.g., zinc, magnesium, aluminum, and titanium) salts of these aromatic carboxylic acids; phenol resin color-developing agents such as p-phenylphenol-formalin resins and p-butylphenol-acetylene resins, and mixtures of these phenol resin color-developing agents and the metal salts of the aromatic carboxylic acids.

Paper, synthetic paper, a film, a plastic film, a foamed plastic film, nonwoven cloth, recycled paper (e.g., recycled paper pulps), or the like, conventionally known can be used as the support used in the present invention. Moreover, the combination thereof can also be used as the support.

Examples of methods for forming a recording material layer on the support include a method comprising applying a dispersion solution containing a dispersion solution of a color-forming compound, a dispersion solution of a color-developing agent, and a dispersion solution of a filler to a support, followed by drying, a method comprising spraying such a dispersion solution onto a support with a spray or the like, followed by drying, and a method comprising dipping a support in such a dispersion solution for a given time, followed by drying. Moreover, examples of the application method include hand coating, a size press coater method, a roll coater method, an air knife coater method, a blend coater method, a flow coater method, a curtain coater method, a comma direct method, a gravure direct method, a gravure reverse method, and a reverse roll coater method.

EXAMPLES

Hereinafter, a recording material of the present invention will be described in detail with reference to Examples. However, the present invention is not necessarily limited to them.

Example 1

Acetic Acid Form 300 g (1.2 mol) of 4,4'-dihydroxydiphenylsulfone (hereinafter, referred to as BPS) and 100 g (2.4 mol) of sodium hydroxide were dissolved in 180 g of water. Into the solution, 6.5 g (0.05 mol) of dichloroacetic acid was added dropwise at room temperature over 10 minutes. After the completion of the dropwise addition, the reaction mixture was heated and reacted under reflux for 3 hours. After the completion of the reaction, the reaction solution was cooled to room temperature, and hydrochloric acid was added dropwise thereto until the reaction solution became neutral. Then, sodium bicarbonate was added thereto until the pH of the reaction solution became around 9. The reaction solution was heated to 70° C. The reaction solution was continuously stirred at 70° C. for 30 minutes and then cooled to room temperature. The deposited BPS crystals were filtered off. The filtrate was subjected to extraction with methyl isobutyl ketone (hereinafter, referred to as MIBK), and the solvent in the MIBK solution was distilled off under reduced pressure to obtain 23.8 g of 1,1-bis(4-(4-hydroxyphenylsulfonyl)phenoxy)acetic acid (No. 1 compound (a=1) in Table 1, 0.043 mol). Melting point: 270-274° C. (decomp.)

$^1$HNMR (d6-DMSO, δ ppm): 5.93 (s, 1H), 6.30 (d, 4H), 7.08 (d, 4H), 7.32 (d, 4H), 7.64 (d, 4H)

Example 2

Methyl Ester Form 4.5 g of 1,1-bis(4-(4-hydroxyphenylsulfonyl)phenoxy) acetic acid synthesized in Example 1 was dissolved in 50 ml of methanol. To the solution, one drop of concentrated sulfuric acid was added at room temperature. The reaction solution was heated and reacted under reflux for 1 hour. Then, the solvent was distilled off under reduced pressure to obtain 1,1-bis(4-(4-hydroxyphenylsulfonyl)phenoxy)acetic acid methyl ester. The obtained crude crystals were recrystallized from n-hexane/ethyl acetate to obtain purified crystals of 1,1-bis(4-(4-hydroxyphenylsulfonyl)phenoxy)acetic acid methyl ester (No. 2 compound (a=1) in Table 1, melting point: 213-215° C.) (yield based on the acetic acid form: 90%).

$^1$H-NMR (d6-acetone, δ ppm): 3.80 (s, 3H), 6.63 (s, 1H), 6.99 (d, 4H), 7.24 (d, 4H), 7.75 (d, 4H), 7.90 (d, 4H)

Example 3 n-Propyl Ester Form

The compound was synthesized (No. 4 compound (a=1) in Table 1, melting point: 83-84° C.) by the method described in Example 2 except that n-propanol was used instead of methanol of Example 2.

$^1$H-NMR (d6-acetone, δ ppm): 0.76 (t, 3H), 1.56 (m, 2H), 4.15 (t, 2H), 6.65 (s, 1H), 6.99 (d, 4H), 7.26 (d, 4H), 7.80 (d, 4H), 7.90 (d, 4H)

Example 4 n-Butyl Ester Form

The compound was synthesized (No. 6 compound (a=1) in Table 1, melting point: 81-82° C.) by the method described in Example 2 except that n-butanol was used instead of methanol of Example 2.

$^1$H-NMR (d6-acetone, δ ppm): 0.77 (t, 3H), 1.20 (m, 2H), 1.52 (m, 2H), 4.20 (t, 2H), 6.65 (s, 1H), 6.95 (d, 4H), 7.26 (d, 4H), 7.80 (d, 4H), 7.90 (d, 4H)

Example 5

Allyl Ester Form

The compound was synthesized (No. 22 compound (a=1) in Table 1, melting point: 73-74° C.) by the method described in Example 2 except that allyl alcohol was used instead of methanol of Example 2.

$^1$H-NMR (d6-acetone, δ ppm): 4.71 (d, 2H), 5.14 (dd, 1H), 5.37 (dd, 1H), 5.83 (ddd, 1H), 6.67 (s, 1H), 6.99 (d, 4H), 7.24 (d, 4H), 7.75 (d, 4H), 7.90 (d, 4H)

Example 6

Isopropyl Ester Form

The compound was synthesized (No. 5 compound (a=1) in Table 1, melting point: 193-194° C.) by the method described in Example 2 except that isopropyl alcohol was used instead of methanol of Example 2.

$^1$H-NMR (d6-acetone, δ ppm): 1.12 (d, 6H), 5.04 (q, 1H), 6.57 (s, 1H), 6.98 (d, 4H), 7.26 (d, 4H), 7.79 (d, 4H), 7.90 (d, 4H)

Example 7

Diallylamide Form 25.0 g (0.1 mol) of BPS and 13.8 g (0.1 mol) of potassium carbonate were added into 200 ml of dimethylformamide, and the mixture was heated to 110° C. Then, 1.7 g (0.0083 mol) of N,N-diallyl-2,2-dichloroacetamide was added dropwise thereto. After the completion of the dropwise addition, the reaction mixture was reacted for 6 hours with the temperature unchanged. After the completion of the reaction, the reaction solution was cooled to 60° C., and 120 ml of water was added thereto. The pH of the solution was adjusted to 4.0 with 10% hydrochloric acid, and the deposited crystals were filtered under reduced pressure. The obtained crystals were recrystallized from methanol/water to obtain approximately 6.2 g of the compound of interest.

The obtained crystals and 6.2 g (0.078 mol) of pyridine were added into 50 ml of methylene chloride, and the mixture was stirred under ice cooling. 2.8 g (0.028 mol) of acetic anhydride was added dropwise thereto, and then, the reaction mixture was reacted at room temperature for 1 hour. The reaction solution was washed with dilute hydrochloric acid, and then, the solvent in the organic layer was distilled off under reduced pressure. The residue was purified by silica gel column chromatography (chloroform/acetone=100/2). The solvent in the eluate was distilled off under reduced pressure, and the residue was dissolved in 30 ml of methanol. To the solution, an aqueous caustic soda solution was then added, and the reaction mixture was reacted at room temperature. After the completion of the reaction, dilute hydrochloric acid was added to the reaction solution, and the deposited crystals were filtered off. The crystals were dried under reduced pressure to obtain 1.8 g of the compound of interest (No. 151 compound (a=1) in Table 1, melting point: 104-105° C.).

$^1$H-NMR (d6-acetone, δ ppm): 3.94 (d, 2H), 4.16 (d, 2H), 5.07 (m, 2H), 5.17 (m, 2H), 5.67 (m, 1H), 5.82 (m, 1H), 6.69 (s, 1H), 6.99 (d, 4H), 7.22 (d, 4H), 7.80 (d, 4H), 7.90 (d, 4H)

Example 8

Diethylamide Form 1.9 g of the compound was synthesized (No. 132 compound (a=1) in Table 1, melting point: 115-117° C.) by the method described in Example 7 except that 3.1 g (0.0167 mol) of N,N-diethyl-2,2-dichloroacetamide was used instead of N,N-diallyl-2,2-dichloroacetamide of Example 7, and 50 g (0.2 mol) of BPS, 27.6 g (0.2 mol) of potassium carbonate, 400 ml of dimethylformamide, and 3.1 g (0.0167 mol) of N,N-diallyl-2,2-dichloroacetamide were used.

$^1$H-NMR (d6-acetone, δ ppm): 0.90 (t, 3H), 1.06 (t, 3H), 3.24 (q, 2H), 3.46 (q, 1H), 6.51 (s, 1H), 6.87 (d, 4H), 7.10 (d, 4H), 7.68 (d, 4H), 7.77 (d, 4H)

Example 9

Methylphenylamide Form 2.4 g of the compound was synthesized (No. 174 compound (a=1) in Table 1, melting point: 129-130° C.) by the method described in Example 8 except that 3.6 g (0.0167 mol) of N-ethyl-N-phenyl-2,2-dichloroacetamide was used instead of N,N-diethyl-2,2-dichloroacetamide of Example 8.

$^1$H-NMR (d6-acetone, δ ppm): 3.29 (s, 3H), 6.22 (s, 1H), 6.98 (dd, 8H), 7.20-7.49 (m, 5H), 7.78 (dd, 8H)

Example 10

Morpholinoamide Form 1.7 g of the compound was synthesized (No. 193 compound (a=1) in Table 1, melting point: 150-152° C.) by the method described in Example 8 except that 3.3 g (0.0167 mol) of morpholino-2,2-dichloroacetamide was used instead of N,N-diethyl-2,2-dichloroacetamide of Example 8.

$^1$H-NMR (d6-acetone, δ ppm): 3.55-3.72 (m, 8H), 6.95 (d, 4H), 6.80 (s, 1H), 7.23 (d, 4H), 7.77 (d, 4H), 7.89 (d, 4H)

Example 11

Preparation of Thermal Recording Paper

| Dispersion solution of color-forming compound (solution A) | |
|---|---|
| 3-di-n-butylamino-6-methyl-7-anilinofluoran | 16 parts |
| 10% aqueous solution of polyvinyl alcohol | 84 parts |
| Dispersion solution of color-developing agent (solution B) | |
| Compound of Example 2 | 16 parts |
| 10% aqueous solution of polyvinyl alcohol | 84 parts |
| Dispersion solution of filler (solution C) | |
| Calcium carbonate | 27.8 parts |
| 10% aqueous solution of polyvinyl alcohol | 26.2 parts |
| Water | 71 parts |

(parts: parts by mass)

Each mixture having the composition of the solution A, B, or C was sufficiently ground with a sand grinder to prepare dispersion solutions of the components of the solutions A to C. 1 part by mass of the solution A, 2 parts by mass of the solution B, and 4 parts by mass of the solution C were mixed to prepare a coating solution. This coating solution was applied to white paper using a wire rod (manufactured by Webster, Wire Bar No. 12), and the paper was dried. Then, calendering treatment was performed to prepare thermal recording paper (coating solution: approximately 5.5 g/m$^2$ in terms of dry mass).

Examples 12 to 18

Thermal paper was prepared by the method described in Example 11 except that the compounds of Examples 3 to 9 were used instead of the compound of Example 2 in the dispersion solution of the color-developing agent (solution B) of Example 11.

Comparative Example 1

Thermal paper was prepared by the method described in Example 11 except that 4-hydroxy-4'-isopropoxydiphenylsulfone was used instead of the compound of Example 2 in the dispersion solution of the color-developing agent (solution B) of Example 11.

|   | Color-developing agent | No. described in Table 1 |
|---|---|---|
| Example 11 | Compound of Example 2 | No. 2 (a = 1) |
| Example 12 | Compound of Example 3 | No. 4 (a = 1) |
| Example 13 | Compound of Example 4 | No. 6 (a = 1) |
| Example 14 | Compound of Example 5 | No. 22 (a = 1) |
| Example 15 | Compound of Example 6 | No. 5 (a = 1) |
| Example 16 | Compound of Example 7 | No. 151 (a = 1) |
| Example 17 | Compound of Example 8 | No. 132 (a = 1) |
| Example 18 | Compound of Example 9 | No. 174 (a = 1) |
| Comparative Example 1 | 4-hydroxy-4'-isopropoxydiphenylsulfone | |

Test Example 1

Evaluation on Heat Resistance of Background

Each test paper was subjected to a stability test under conditions shown below before and after a test. The results are summarized in Table 3.

Before Test

A portion of each thermal recording paper prepared in Examples 11 to 18 and Comparative Example 1 was cut off, and the optical concentration of the background was measured using a Macbeth reflection densitometer (filter used: #106).

Heat Resistance Test

A portion of each thermal recording paper prepared in Examples 11 to 18 and Comparative Example 1 was cut off and kept in a thermostat (trade name: DK-400, manufactured by Yamato Scientific Co., Ltd) at a temperature of 110° C. for 24 hours. The optical concentration of the background after being kept was measured using a Macbeth reflection densitometer (filter used: #106).

TABLE 3

Evaluation results of test on heat resistance of background

|   | Before test | After heat resistance test |
|---|---|---|
| Example 11 | 0.10 | ⊙ |
| Example 12 | 0.16 | ⊙ |
| Example 13 | 0.16 | ○ |
| Example 14 | 0.17 | ⊙ |
| Example 15 | 0.14 | ⊙ |
| Example 16 | 0.10 | ⊙ |
| Example 17 | 0.09 | ⊙ |
| Example 18 | 0.14 | ○ |
| Comparative Example 1 | 0.10 | ○ |

⊙: Practically good
○: Slightly poor, but practically no problem
Δ: Having a practical problem
X: Cannot be used practically The results of Table 3 demonstrated that the heat resistance of the background was good.

Test Example 2

Test on Storage Stability of Image

Each test paper was subjected to a stability test under conditions shown below. The results are summarized in Table 4.

Before Test

A portion of each thermal recording paper prepared in Examples 11 to 18 and Comparative Example 1 was cut off and colored under conditions involving 0.72 mj per dot using a thermal printing tester (trade name: model TH-PMH, manufactured by Ohkura Electric Co., Ltd.). The concentration of the colored image was measured using a Macbeth reflection densitometer (filter used: #106).

Light Resistance Test

A portion of each colored thermal recording paper was cut off and subjected to a light resistance test using a light resistance tester (trade name: UV Long-Life Fade Meter model U48, manufactured by Suga Test Instruments Co., Ltd.). After 12 hours, the concentration of the background was measured using a Macbeth reflection densitometer (filter used: #106).

Heat Resistance Test

A portion of each colored thermal recording paper was cut off and subjected to a heat resistance test in a thermostat (trade name: DK-400, manufactured by Yamato Scientific Co., Ltd) at a temperature of 100° C. After 24 hours, the concentration of the colored image was measured using a Macbeth reflection densitometer (filter used: #106).

Plasticizer Resistance Test

A portion of each colored thermal recording paper was cut off, and water was added dropwise thereto. A nylon film (commercially available product) was put on the surface. After 48 hours at 40° C. under a load of 0.0294 MPa (300 gf/cm$^2$), the concentration of the colored image was measured using a Macbeth reflection densitometer (filter used: #106).

TABLE 4

Evaluation results of test on image stability

|   | Before test | Light resistance test | Heat resistance test | Plasticizer resistance test |
|---|---|---|---|---|
| Example 11 | 1.02 | ⊙ | ○ | ⊙ |
| Example 12 | 0.98 | ⊙ | ○ | ⊙ |
| Example 13 | 1.15 | ⊙ | ○ | ⊙ |
| Example 14 | 0.73 | ⊙ | ○ | ⊙ |
| Example 15 | 1.10 | ⊙ | ○ | ⊙ |
| Example 16 | 1.21 | ⊙ | ○ | ⊙ |
| Example 17 | 1.18 | ⊙ | ○ | ⊙ |
| Example 18 | 1.10 | ○ | ○ | ⊙ |
| Comparative Example 1 | 1.40 | ○ | ○ | ○ |

⊙: Practically good
○: Slightly poor, but practically no problem
Δ: Having a practical problem
X: Cannot be used practically The results of Table 4 demonstrated that the light resistance and plasticizer resistance of the image were particularly good although the heat resistance of the image was fully comparable to Comparative Example 1.

Example 19

Carboxylic Acid Form 16.6 g (0.4 mol) of caustic soda was dissolved in 30 ml of water. To the solution, 50.0 g (0.2 mol) of 4,4'-BPS was added. The mixture was heated to 90° C. Then, 15.1 g (0.1 mol) of dichloroacetic acid sodium salt was added thereto, and the mixture was reacted at 100° C. for 2 hours. After the completion of the reaction, the reaction solution was cooled to room temperature, and its pH was adjusted to 4 with 10% hydrochloric acid. The supernatant was discarded by decantation, and then, the residue was dissolved by the addition of a saturated aqueous solution of sodium bicarbonate. Residual 4,4'-BPS was removed by extraction with methyl isobutyl ketone (MIBK). The pH of the aqueous layer was further adjusted to 4 with 10% hydrochloric acid, and the supernatant was discarded by decantation. To the residue, saturated saline was added, and the compound of interest was extracted with THF. The solvent was distilled off under reduced pressure to obtain 48.0 g of the amorphous compound of interest.

$^1$H-NMR (d6-DMSO, δ ppm): 3.78 (s, 3H), 6.90 (dd, 4H), 7.20 (dd, 4H), 7.73 (dd, 4H), 7.89 (dd, 4H)

Moreover, as a result of analyzing the obtained reaction product by high-performance liquid chromatography, it had the following composition:

| Retention time (min) | Area ratio (A %) |
| --- | --- |
| 2.70 | 44.5 |
| 5.99 | 30.1 |
| 12.04 | 18.5 |
| 23.14 | 8.1 |

Example 20

Methyl Ester Form 12.5 g (0.05 mol) of the compound synthesized in Example 19, 6.9 g (0.05 mol) of methanol, and 4.37 g (0.025 mol) of concentrated sulfuric acid were placed in a reaction vessel and reacted at 100° C. for 3 hours. After the completion of the reaction, the reaction solution was cooled to room temperature and poured into a saturated aqueous solution of sodium bicarbonate. The deposited crystals were filtered and dried under reduced pressure to obtain 8.3 g of the compound of interest as white crystals. The obtained reaction product had a melting point of 148 to 150° C. and had the following composition as a result of analysis by high-performance liquid chromatography:

| Retention time (min) | Area ratio (A %) |
| --- | --- |
| 1.88 | 49.8 |
| 2.40 | 26.1 |
| 3.20 | 10.7 |
| 4.35 | 4.3 |
| 5.97 | 1.5 |

Example 21

Ethyl Ester Form

The compound was synthesized (melting point: 107-110° C.) by the method described in Example 20 except that ethanol was used instead of methanol of Example 20. Moreover, the compound had the following composition as a result of analysis by high-performance liquid chromatography:

| Retention time (min) | Area ratio (A %) |
| --- | --- |
| 2.03 | 51.2 |
| 3.00 | 26.5 |
| 4.81 | 11.6 |
| 8.07 | 4.7 |
| 13.63 | 1.6 |

Example 22

Diethylamide Form 25.0 g (0.1 mol) of 4,4'-BPS and 13.8 g (0.1 mol) of potassium carbonate were added into 200 ml of N,N-dimethylformamide (DMF), and the mixture was stirred at 110° C. 7.9 g (0.05 mol) of dichloroacetic acid diethylamide was added thereto, and the mixture was reacted at 110° C. for 9 hours. The reaction mixture was cooled to room temperature, and then, the solvent was distilled off under reduced pressure. To the concentrated residue, 400 ml of water was added, and the pH of the reaction solution was adjusted to 4 with 20% hydrochloric acid. The deposited crystals were filtered off. The crystals were dissolved in 155 g of a 3% aqueous solution of caustic soda. To the solution, 380 ml of water and 227 g of methanol were then added. Then, the pH of the reaction solution was adjusted to 4 with dilute hydrochloric acid, and the deposited crystals were filtered off and dried under reduced pressure to obtain 17 g of the compound of interest as white crystals. The obtained reaction product had a melting point of 135 to 140° C.

$^1$H-NMR (d6-DMSO, δ ppm): 0.98 (bs, 3H), 1.11 (bs, 3H), 3.35 (dd, 4H), 6.91 (dd, 4H), 7.19 (bs, 4H), 7.74 (dd, 4H), 7.88 (dd, 4H)

Moreover, the compound had the following composition as a result of analysis by high-performance liquid chromatography:

| Retention time (min) | Area ratio (A %) |
| --- | --- |
| 1.98 | 24.4 |
| 2.81 | 20.0 |
| 4.30 | 14.2 |
| 6.91 | 10.1 |
| 11.38 | 7.1 |
| 18.92 | 4.5 |
| 31.60 | 2.6 |

Example 23

Diallylamide Form 21.4 g of the compound was synthesized (melting point: 115-118° C.) by the method described in Example 22 except that 10.4 g of dichloroacetic acid diallylamide was used instead of dichloroacetic acid diethylamide of Example 22. Moreover, the compound had the following composition as a result of analysis by high-performance liquid chromatography:

| Retention time (min) | Area ratio (A %) |
| --- | --- |
| 2.25 | 24.1 |
| 4.09 | 21.4 |
| 8.51 | 15.9 |
| 18.78 | 11.3 |
| 41.93 | 7.6 |

Example 24

Phenylmethylamide Form 20.6 g of the compound was synthesized (melting point: 155-158° C.) by the method described in Example 22 except that 10.9 g of dichloroacetic acid phenylmethylamide was used instead of dichloroacetic acid diethylamide of Example 22. Moreover, the compound had the following composition as a result of analysis by high-performance liquid chromatography:

| Retention time (min) | Area ratio (A %) |
|---|---|
| 2.03 | 17.3 |
| 3.01 | 16.5 |
| 4.84 | 14.2 |
| 8.20 | 12.6 |
| 14.26 | 8.7 |
| 25.04 | 5.6 |
| 45.35 | 3.5 |

Example 25

Preparation of Thermal Recording Paper

| Dispersion solution of color-forming compound (solution A) | |
|---|---|
| 3-di-n-butylamino-6-methyl-7-anilinofluoran | 16 parts |
| 10% aqueous solution of polyvinyl alcohol | 84 parts |
| Dispersion solution of color-developing agent (solution B) | |
| Composition of Example 20 | 16 parts |
| 10% aqueous solution of polyvinyl alcohol | 84 parts |
| Dispersion solution of filler (solution C) | |
| Calcium carbonate | 27.8 parts |
| 10% aqueous solution of polyvinyl alcohol | 26.2 parts |
| Water | 71 parts |

(parts: parts by mass)

Each mixture having the composition of the solution A, B, or C was sufficiently ground with a sand grinder to prepare dispersion solutions of the components of the solutions A to C. 1 part by mass of the solution A, 2 parts by mass of the solution B, and 4 parts by mass of the solution C were mixed to prepare a coating solution. This coating solution was applied to white paper using a wire rod (manufactured by Webster, Wire Bar No. 12), and the paper was dried. Then, calendering treatment was performed to prepare thermal recording paper (coating solution: approximately 5.5 g/m$^2$ in terms of dry mass).

Example 26

Thermal paper was prepared by the method described in Example 25 except that the composition of Example 21 was used instead of the composition of Example 20 in the dispersion solution of the color-developing agent (solution B) of Example 25.

Comparative Example 2

Thermal paper was prepared by the method described in Example 25 except that D-90 (manufactured by Nippon Soda Co., Ltd.) was used instead of the composition of Example 20 in the dispersion solution of the color-developing agent (solution B) of Example 25.

Test Example 3

Evaluation on Heat Resistance of Background

Each test paper was subjected to a stability test under conditions shown below before and after a test. The results are summarized in Table 5.
Before Test
A portion of each thermal recording paper prepared in Examples 25 and 26 and Comparative Example 2 was cut off, and the optical concentration of the background was measured using a Macbeth reflection densitometer (filter used: #106).
Heat Resistance Test
A portion of each thermal recording paper prepared in Examples 25 and 26 and Comparative Example 2 was cut off and kept in a thermostat (trade name: DK-400, manufactured by Yamato Scientific Co., Ltd) at a temperature of 110° C. for 24 hours. The optical concentration of the background after being kept was measured using a Macbeth reflection densitometer (filter used: #106).

TABLE 5

| Evaluation results of heat resistance of background | | |
|---|---|---|
| | Before test | Heat resistance test |
| Example 25 | 0.12 | ⊙ |
| Example 26 | 0.11 | ○ |
| Comparative Example 2 | 0.06 | ○ |

⊙: Practically good
○: Slightly poor, but practically no problem
Δ: having a practical problem
X: Cannot be used practically The results of Table 5 demonstrated that the heat resistance of the background was good.

Test Example 4

Image Stability Test

Each test paper was subjected to a stability test under conditions shown below. The results are summarized in Table 6.
Before Test
A portion of each thermal recording paper prepared in Examples 25 and 26 and Comparative Example 2 was cut off and colored under conditions involving 0.72 mj per dot using a thermal printing tester (trade name: model TH-PMH, manufactured by Ohkura Electric Co., Ltd.). The concentration of the colored image was measured using a Macbeth reflection densitometer (filter used: #106).
Moist Heat Resistance Test
A portion of colored thermal recording paper was cut off and subjected to a moist heat resistance test in a low-temperature thermohygrostat (trade name: THN050FA, manufactured by ADVANTEC Toyo Kaisha, Ltd.) under conditions involving 50° C. and 80% humidity. After 24 hours, the concentration of the colored image was measured using a Macbeth reflection densitometer (filter used: #106).
Light Resistance Test
A portion of each colored thermal recording paper was cut off and subjected to a light resistance test using a light resistance tester (trade name: UV Long-Life Fade Meter model U48, manufactured by Suga Test Instruments Co., Ltd.). After 12 hours, the concentration of the image was measured using a Macbeth reflection densitometer (filter used: #106).
Heat Resistance Test
A portion of each colored thermal recording paper was cut off and subjected to a heat resistance test in a thermostat (trade name: DK-400, manufactured by Yamato Scientific Co., Ltd) at a temperature of 100° C. After 24 hours, the concentration of the colored image was measured using a Macbeth reflection densitometer (filter used: #106).
Oil Resistance Test
A portion of each colored thermal recording paper was cut off and dipped in cooking oil. After 24 hours at room temperature, the concentration of the colored image was measured using a Macbeth reflection densitometer (filter used: #106).

Plasticizer Resistance Test

A portion of each colored thermal recording paper was cut off, and water was added dropwise thereto. A nylon film (commercially available product) was put on the surface. After 48 hours at 40° C. under a load of 0.0294 MPa (300 gf/cm$^2$), the concentration of the colored image was measured using a Macbeth reflection densitometer (filter used: #106).

Water Resistance Test

A portion of each colored thermal recording paper was cut off and dipped in water. After 24 hours at room temperature, the concentration of the colored image was measured using a Macbeth reflection densitometer (filter used: #106).

TABLE 6

Evaluation results of image stability

| | Before test | Moist heat resistance test | Light resistance test | Heat resistance test | Oil resistance test | Plasticizer resistance test | Water resistance test |
|---|---|---|---|---|---|---|---|
| Example 25 | 1.09 | ⊚ | ⊚ | ⊚ | ⊚ | ○ | ○ |
| Example 26 | 1.17 | ⊚ | ⊚ | ⊚ | ⊚ | ○ | ○ |
| Comparative Example 2 | 1.12 | ⊚ | ⊚ | ⊚ | ⊚ | ⊚ | ⊚ |

⊚: Practically good
○: Slightly poor, but practically no problem
Δ: Having a practical problem
X: Cannot be used practically The results of Table 6 demonstrated that although there existed a sample inferior in the plasticizer resistance of the image to Comparative Example 2, the other image stabilities were totally comparable thereto.

Test Example 5

Thermal Responsiveness

Static Color-Developing Sensitivity

A portion of each thermal recording paper prepared in Examples 25 and 26 and Comparative Example 2 was cut off and colored under conditions involving 0.72 mj per dot using a thermal printing tester (trade name: model TH-PMH, manufactured by Ohkura Electric Co., Ltd.). The concentration of the colored image was measured using a Macbeth reflection densitometer (filter used: #106).

Dynamic Color-Developing Sensitivity

A portion of each thermal recording paper prepared in Examples 25 and 26 and Comparative Example 2 was cut off and subjected to a dynamic color-developing sensitivity test using a thermal printing tester (trade name: model TH-PMH, manufactured by Ohkura Electric Co., Ltd.). The portion was colored under conditions involving a printing voltage of 17 V and respective pulse widths of 0.2, 0.35, 0.5, 0.65, 0.8, 0.95, 1.1, 1.25, 1.4, 1.6, and 1.8 ms. Then, the concentration of the print was measured using a Macbeth reflection densitometer (filter used: #106).

TABLE 7

Evaluation results of thermal responsiveness

| | Static color-developing sensitivity | Dynamic color-developing sensitivity |
|---|---|---|
| Example 25 | ○ | ○ |
| Example 26 | ⊚ | ⊚ |
| Comparative Example 2 | ○ | ○ |

⊚: Practically good
○: Slightly poor, but practically no problem
Δ: Having a practical problem
X: Cannot be used practically The results of Table 7 demonstrated that the thermal responsiveness was good.

The comprehensive assessment of the results described above showed that the samples of Examples 25 and 26 were almost functionally equivalent to the sample of Comparative. Example 2 and were, however, particularly excellent in the heat resistance of the background or thermal responsiveness.

INDUSTRIAL APPLICABILITY

A recording material excellent in background and image stabilities and a novel compound that can be used therein can be provided.

The invention claimed is:

1. A compound represented by formula (I):

$$\left\{R^{41}O-\underset{(R^{11})_n}{\underset{|}{\bigcirc}}-S(O)_m-\underset{(R^{12})_p}{\underset{|}{\bigcirc}}-O-\underset{\underset{O}{\overset{R^2}{C}}}{\overset{R^2}{\underset{|}{C}}}-O-\underset{(R^{13})_q}{\underset{|}{\bigcirc}}-S(O)_m-\underset{(R^{14})_r}{\underset{|}{\bigcirc}}-OR^{42}\right\}_a \quad (I)$$

[wherein $R^{11}$ to $R^{14}$ each independently represent a halogen atom, a $C_1$-$C_6$ alkyl group, or a $C_2$-$C_6$ alkenyl group; n, p, q, and r each independently represent 0 or any integer of 1 to 4; m represents 0 or any integer of 1 to 2; a represents any integer of 1 to 10; $R^2$ represents a hydrogen atom or a $C_1$-$C_6$ alkyl group; $R^3$ represents a hydroxy group, an $OR^{51}$ group, a $NR^{52}R^{53}$ group, a $SR^{54}$ group, or OM; $R^{51}$ represents a $C_1$-$C_6$ alkyl group, a $C_2$-$C_6$ alkenyl group, an optionally substituted phenyl group, or an optionally substituted benzyl group; $R^{52}$ to $R^{54}$ each represent a hydrogen atom, a $C_1$-$C_6$ alkyl group, a $C_2$-$C_6$ alkenyl group, an optionally substituted phenyl group, or an optionally substituted benzyl group, and $R^{52}$ and $R^{53}$ together optionally form a saturated or unsaturated $C_4$-$C_{10}$ ring, which, optionally, further comprises at least one heteroatom selected from S, N, and O; M represents a metal atom; and $R^{41}$ and $R^{42}$ each independently represent a hydrogen atom, a $C_1$-$C_6$ alkyl group, a $C_2$-$C_6$ alkenyl group, or a protective group for the hydroxy group].

2. The compound according to claim 1, wherein the compound represented by formula (I) is represented by formula (II):

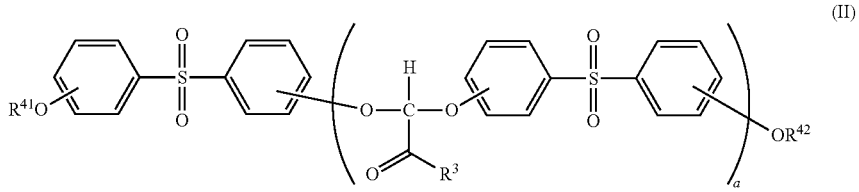

[wherein a represents any integer of 1 to 10; $R^3$ represents a hydroxy group, an $OR^{51}$ group, a $NR^{52}R^{53}$ group, a $SR^{54}$ group, or OM; $R^{51}$ represents a $C_1$-$C_6$ alkyl group, a $C_2$-$C_6$ alkenyl group, an optionally substituted phenyl group, or an optionally substituted benzyl group; $R^{52}$ to $R^{54}$ each represent a hydrogen atom, a $C_1$-$C_6$ alkyl group, a $C_2$-$C_6$ alkenyl group, an optionally substituted phenyl group, or an optionally substituted benzyl group, and $R^{52}$ and $R^{53}$ together optionally form a saturated or unsaturated $C_4$-$C_{10}$ ring, which, optionally, further comprises at least one heteroatom selected from S, N, and O; M represents a metal atom; and $R^{41}$ and $R^{42}$ each independently represent a hydrogen atom, a $C_1$-$C_6$ alkyl group, a $C_2$-$C_6$ alkenyl group, or a protective group for the hydroxy group].

3. A recording material containing a color-forming compound and at least one compound according to claim 1.

4. A composition containing two or more compounds represented by formula (I), the compounds differing in a:

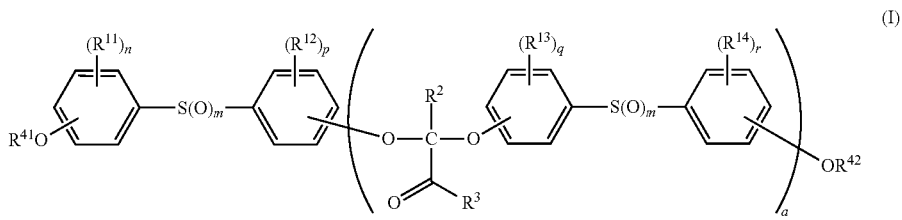

[wherein $R^{11}$ to $R^{14}$ each independently represent a halogen atom, a $C_1$-$C_6$ alkyl group, or a $C_2$-$C_6$ alkenyl group; n, p, q, and r each independently represent 0 or any integer of 1 to 4; m represents 0 or any integer of 1 to 2; a represents any integer of 1 to 10; $R^2$ represents a hydrogen atom or a $C_1$-$C_6$ alkyl group; $R^3$ represents a hydroxy group, an $OR^{51}$ group, a $NR^{52}R^{53}$ group, a $SR^{54}$ group, or OM; $R^{51}$ represents a $C_1$-$C_6$ alkyl group, a $C_2$-$C_6$ alkenyl group, an optionally substituted phenyl group, or an optionally substituted benzyl group; $R^{52}$ to $R^{54}$ each represent a hydrogen atom, a $C_1$-$C_6$ alkyl group, a $C_2$-$C_6$ alkenyl group, an optionally substituted phenyl group, or an optionally substituted benzyl group, and $R^{52}$ and $R^{53}$ together optionally form a saturated or unsaturated $C_4$-$C_{10}$ ring, which, optionally, further comprises at least one heteroatom selected from S, N, and O; M represents a metal atom; and $R^{41}$ and $R^{42}$ each independently represent a hydrogen atom, a $C_1$-$C_6$ alkyl group, a $C_2$-$C_6$ alkenyl group, or a protective group for the hydroxy group].

5. A recording material containing a color-forming compound and at least one composition according to claim 4.

6. A recording sheet having a recording material layer formed from a recording material according to claim 3 or 5 on a support.

7. A reaction composition containing two or more compounds represented by formula (V),

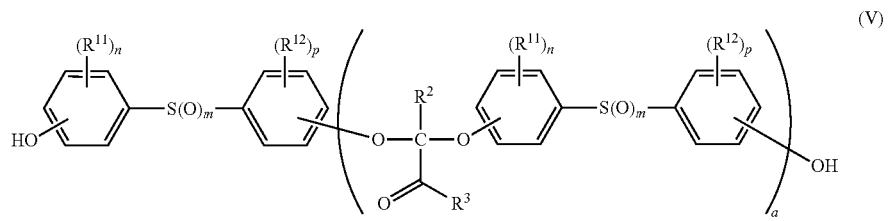

[wherein $R^{11}$ and $R^{12}$ each independently represent a halogen atom, a $C_1$-$C_6$ alkyl group, or a $C_2$-$C_6$ alkenyl group; n and p each independently represent 0 or any integer of 1 to 4; m represents 0 or any integer of 1 to 2; a represents any integer of 1 to 10; $R^2$ represents a hydrogen atom or a $C_1$-$C_6$ alkyl group; $R^3$ represents a hydroxy group, an $OR^{51}$ group, a $NR^{52}R^{53}$ group, a $SR^{54}$ group, or OM; $R^{51}$ represents a $C_1$-$C_6$ alkyl group, a $C_2$-$C_6$ alkenyl group, an optionally substituted phenyl group, or an optionally substituted benzyl group; $R^{52}$ to $R^{54}$ each represent a hydrogen atom, a $C_1$-$C_6$ alkyl group, a $C_2$-$C_6$ alkenyl group, an optionally substituted phenyl group, or an optionally substituted benzyl group, and $R^{52}$ and $R^{53}$ together optionally form a saturated or unsaturated $C_4$-$C_{10}$ ring, which, optionally, further comprises at least one heteroatom selected from S, N, and O; and M represents a metal atom];

the compounds differing in a and being obtained by reacting a compound represented by formula (III)

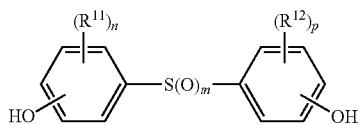 (III)

[wherein $R^{11}$ and $R^{12}$ each independently represent a halogen atom, a $C_1$-$C_6$ alkyl group, or a $C_2$-$C_6$ alkenyl group; n and p each independently represent 0 or any integer of 1 to 4; and m represents 0 or any integer of 1 to 2], with a compound represented by formula (IV):

$$X_2CR^2COR^3 \quad (IV)$$

[wherein each X independently represents a halogen atom; $R^2$ represents a hydrogen atom or a $C_1$-$C_6$ alkyl group; $R^3$ represents a hydroxy group, an $OR^{51}$ group, a $NR^{52}R^{53}$ group, a $SR^{54}$ group, or OM; $R^{51}$ represents a $C_1$-$C_6$ alkyl group, a $C_2$-$C_6$ alkenyl group, an optionally substituted phenyl group, or an optionally substituted benzyl group; $R^{52}$ to $R^{54}$ each represent a hydrogen atom, a $C_1$-$C_6$ alkyl group, a $C_2$-$C_6$ alkenyl group, an optionally substituted phenyl group, or an optionally substituted benzyl group, and $R^{52}$ and $R^{53}$ together optionally form a saturated or unsaturated $C_4$-$C_{10}$ ring, which, optionally, further comprises at least one heteroatom selected from S, N, and O; and M represents a metal atom].

* * * * *